United States Patent
Nicolelis et al.

(10) Patent No.: US 9,943,687 B2
(45) Date of Patent: Apr. 17, 2018

(54) METHOD OF TREATING PARKINSON'S DISEASE AND OTHER MOVEMENT DISORDERS

(75) Inventors: Miguel A. L. Nicolelis, Durham, NC (US); Romulo A. Fuentes, Durham, NC (US)

(73) Assignee: Duke University, Durham, NC (US)

( * ) Notice: Subject to any disclaimer, the term of this patent is extended or adjusted under 35 U.S.C. 154(b) by 402 days.

(21) Appl. No.: 12/733,886

(22) PCT Filed: Sep. 26, 2008

(86) PCT No.: PCT/US2008/011219
§ 371 (c)(1),
(2), (4) Date: Jan. 13, 2011

(87) PCT Pub. No.: WO2009/042217
PCT Pub. Date: Apr. 2, 2009

(65) Prior Publication Data
US 2011/0184489 A1    Jul. 28, 2011

Related U.S. Application Data

(60) Provisional application No. 60/960,356, filed on Sep. 26, 2007.

(51) Int. Cl.
*A61N 1/00* (2006.01)
*A61N 1/36* (2006.01)
*A61N 1/05* (2006.01)

(52) U.S. Cl.
CPC ..... *A61N 1/36025* (2013.01); *A61N 1/36067* (2013.01); *A61N 1/0551* (2013.01); *A61N 1/36003* (2013.01); *A61N 1/3606* (2013.01); *A61N 1/36017* (2013.01); *A61N 1/36064* (2013.01); *A61N 1/36082* (2013.01)

(58) Field of Classification Search
CPC ............. A61N 1/3606; A61N 1/36067; A61N 1/36082; A61N 1/36025; A61N 1/0551; A61N 1/36003
USPC ............................................ 607/1, 2, 45, 46
See application file for complete search history.

(56) References Cited

U.S. PATENT DOCUMENTS

| | | | |
|---|---|---|---|
| 5,602,150 A * | 2/1997 | Lidsky | 514/327 |
| 6,690,974 B2 * | 2/2004 | Archer et al. | 607/45 |
| 2003/0100931 A1 * | 5/2003 | Mullett | 607/46 |
| 2003/0125314 A1 * | 7/2003 | Zusman | 514/185 |
| 2004/0024439 A1 * | 2/2004 | Riso | 607/117 |
| 2004/0181263 A1 | 9/2004 | Balzer et al. | |
| 2005/0065562 A1 * | 3/2005 | Rezai | 607/9 |
| 2005/0182453 A1 | 8/2005 | Whitehurst et al. | |
| 2006/0095088 A1 * | 5/2006 | De Ridder | 607/48 |
| 2006/0161218 A1 | 7/2006 | Danilov | |

(Continued)

OTHER PUBLICATIONS

Taber, Matthew T., and Hans C. Fibiger. "Electrical stimulation of the medial prefrontal cortex increases dopamine release in the striatum." Neuropsychopharmacology 9.4 (1993): 271-275.*

(Continued)

*Primary Examiner* — Lindsey G Wehrheim
(74) *Attorney, Agent, or Firm* — McDonnell Boehnen Hulbert & Berghoff LLP

(57) ABSTRACT

The present invention relates, in general, to movement disorders and, in particular, to a method of treating movement disorders, including Parkinson's Disease.

17 Claims, 20 Drawing Sheets

(56) References Cited

U.S. PATENT DOCUMENTS

| | | |
|---|---|---|
| 2007/0027500 A1 | 2/2007 | Maschino et al. |
| 2007/0049988 A1* | 3/2007 | Carbunaru et al. ............ 607/59 |

OTHER PUBLICATIONS

Supplementary European Search Report issued in connection EP 08833302 dated Sep. 3, 2010.

International Search Report for PCT/US2008/011219, dated Dec. 8, 2008.

Fuentes R, et al. "Spinal cord stimulation restores locomotion in animal models of Parkinson's disease." Science 2009; 323:1578-82.

Fénelon, Gilles, et al. (2011) "Spinal Cord Stimulation for Chronic Pain Improved Motor Function in a Patient with Parkinson's Disease." Parkinsonism & Related Disorders (Aug. 22): 998-1003. doi:10.1016/j.parkreldis.2011.07.015.

Agari, Takashi, et al (2012) "Spinal Cord Stimulation for the Treatment of Abnormal Posture and Gait Disorder in Patients With Parkinson's Disease." Neurologia Medico-Chirurgica 52: 470-474.

Landi, Andrea, et al. (2012) "Spinal Cord Stimulation for the Treatment of Sensory Symptoms in Advanced Parkinson's Disease." Neuromodulation : Journal of the International Neuromodulation Society 2012 (Dec. 10)doi:10.1111/ner.12005.

Hassan, Syed, et al. (2013) "A Patient with Parkinson's Disease Benefits from Spinal Cord Stimulation." Journal of Clinical Neuroscience (Feb. 26) doi:10.1016/j.jocn.2012.08.018.

Arii et al. "Immediate effect of spinal magnetic stimulation on camptocormia in Parkinson's disease" J. Neurol. Neurosurg. Psychiatry 85:1221-1226 (Nov. 2014).

Nicolelis et al. Correspondence to the Editory on "Spinal cord stimulation failed to relieve akinesia or restore locomotion in Parkinson disease" Neurology 75:1484 (Oct. 2010).

Santana et al. "Spinal cord stimulation alleviates motor deficits in a primate model of Parkinson disease" Neuron 84:716-722 (Nov. 2014).

Thevathasan et al. "Spinal cord stimulation failed to relieve akinesia or restore locomotion in Parkinson disease" Neurology 74:1325-1327 (Apr. 2010).

Thevathasan et al. Reply from the authors of "Spinal cord stimulation failed to relieve akinesia or restore locomotion in Parkinson disease" Neurology 75:1484-1485 (Oct. 2010).

Miguel A. L. Nicolelis, MD, PhD Curriculum Vitae (pp. 1-64).

Pinto De Souza et al., "Spinal Cord Stimulation Improves Gait in Patients With Parkinson's Disease Previously Treated With Deep Brain Stimulation," Mov Disord 32(2):278-282 (2017; Epub 2016).

Santana et al., "Spinal Cord Stimulation Alleviates Motor Deficits in a Primate Model of Parkinson's disease," Neuron 19; 84(4): 716-722 (2014).

Yadav et al., "Electrical stimulation of the dorsal columns of the spinal cord for Parkinson's disease," Mov Disord 32(6):820-832 (2017).

* cited by examiner

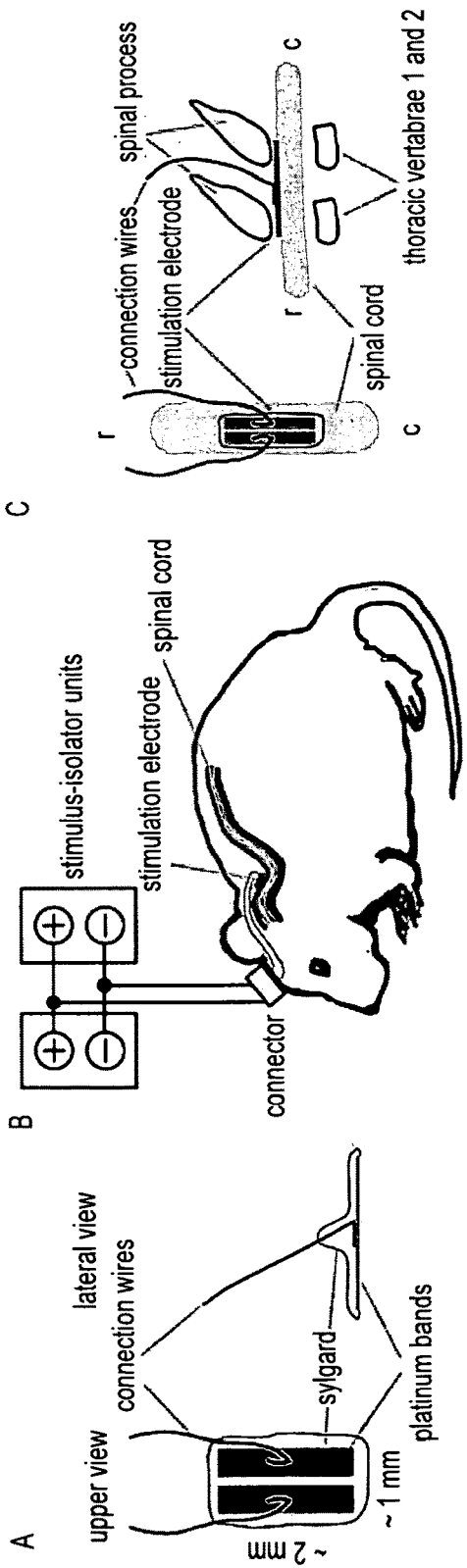

Figure 4. Method for electrical stimulation of posterior funiculi in mice. (A) The stimulation electrode consists of two parallel platinum bands (each 2 mm in length, 0.3 mm in width and 0.025 mm thick) separated ~0.3 mm and embedded in surgical silicone (sylgard). Each band is connected to a wire (Teflon-coated 7-strand stainless steel, 0.001 inches, bare diameter). (B) The electrode is implanted above the dorsal spinal cord and the connections wires are passed subcutaneously to an incision in the head skin and joined to a special connector attached to the skull. The connector is plugged to 2 stimulus-isolator units, which provide biphasic constant-current pulses at desired frequency and intensity. (C) Left: schematic dorsal view of the implanted electrode and the spinal cord. Right: schematic sagittal view of the implanted electrode. The electrode is inserted between vertebrae T1 and T2 and located longitudinally in close proximity to the dorsal surface of the spinal cord, over the posterior funiculi. Both ends of the electrode are trapped between the vertebrae and the spinal cord. r: rostral; c: caudal

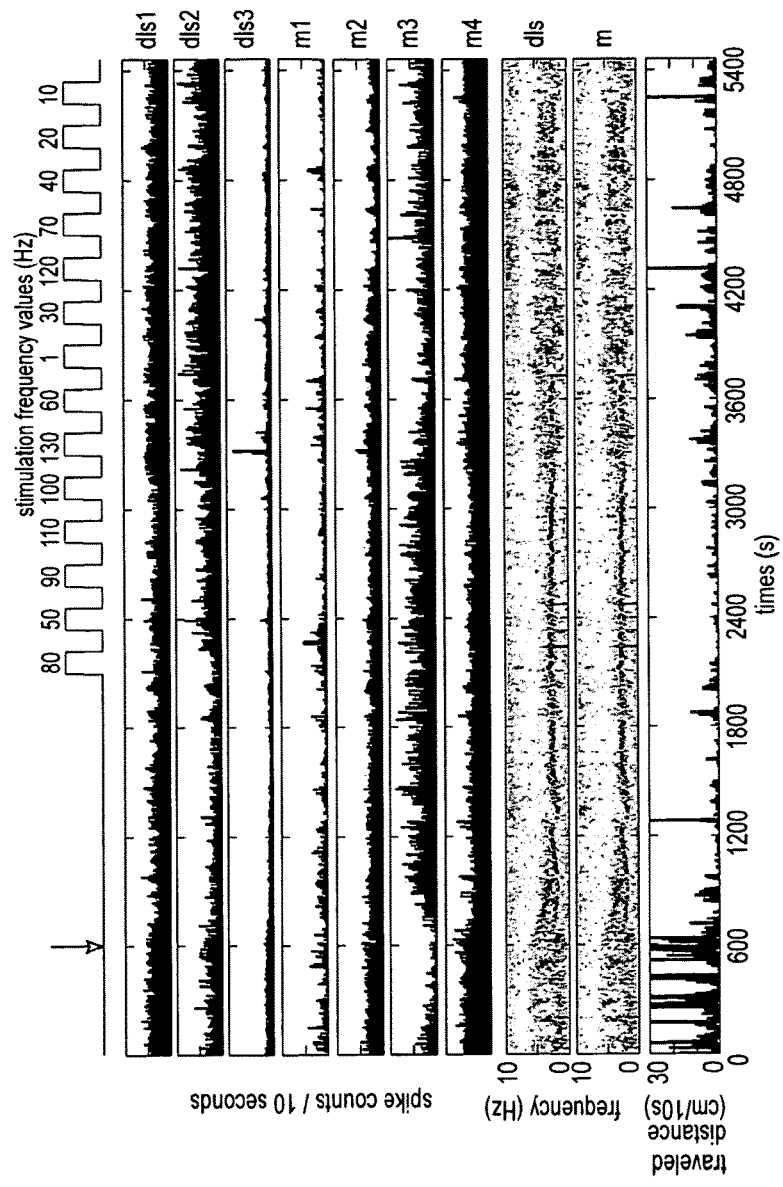

Figure 5. Single neuron and local field potential activity recorded simultaneously with locomotive activity in a mouse partially depleted of dopamine during bilateral electrical stimulation of the infraorbital nerve. Top: Experiment protocol, a step in the black line indicates IS at the specified frequency. Black arrow indicates the AMPT injection. Next 7 panels are the firing rates assessed in 10-second bins for 3 neurons of the dorsolateral striatum (dls1-dls3) and 4 neurons of the primary motor cortex (m1-m4). The next 2 panels are spectrograms, representing the oscillatory power of local field potential (a measure of synchronized activity of neural populations) as function of time in the striatum (dls) and primary motor cortex (m). Warm colors represent high power oscillations. Lower panel represents the traveled distance by the mouse in 10-second periods.

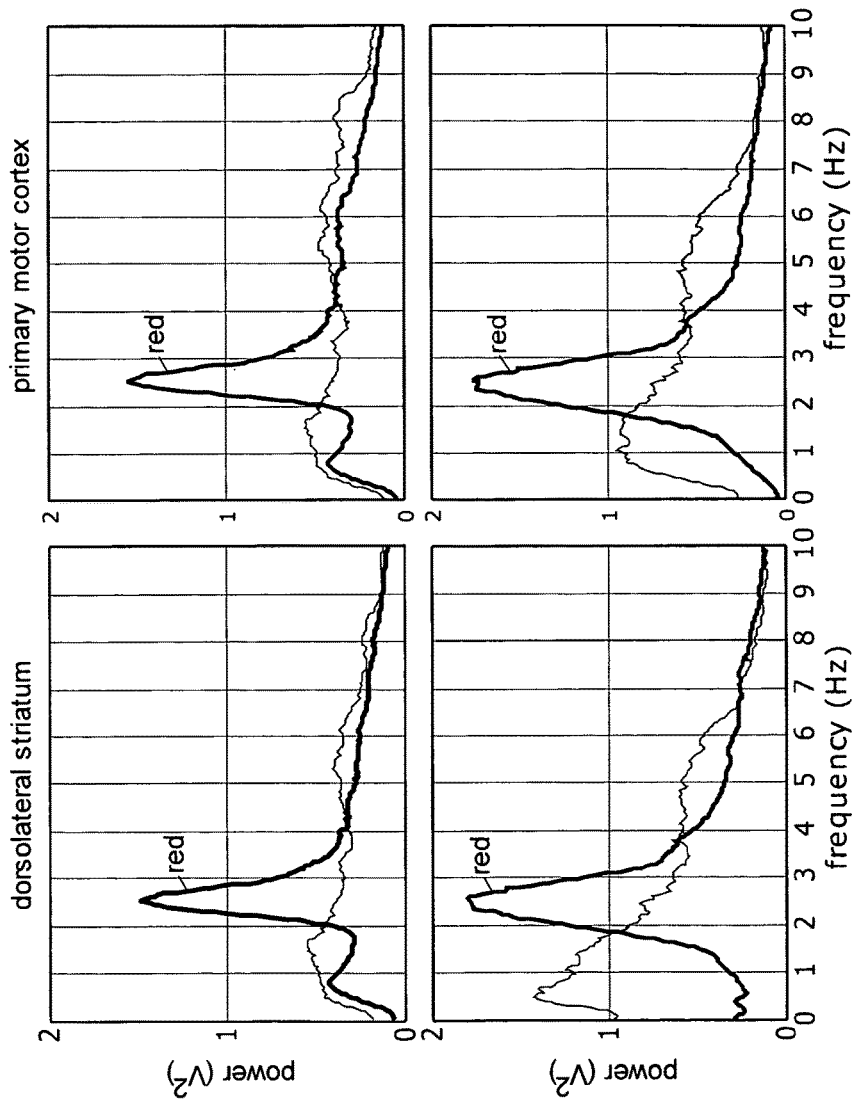
Figure 6. Partial dopamine depletion produces strong synchronization at 4 Hz in the corticostriatal circuit. Blue line is the average power spectra in normal condition; red line is the average power spectra after AMPT injection. Data are from 2 mice (rows). Brain structures indicated on top.

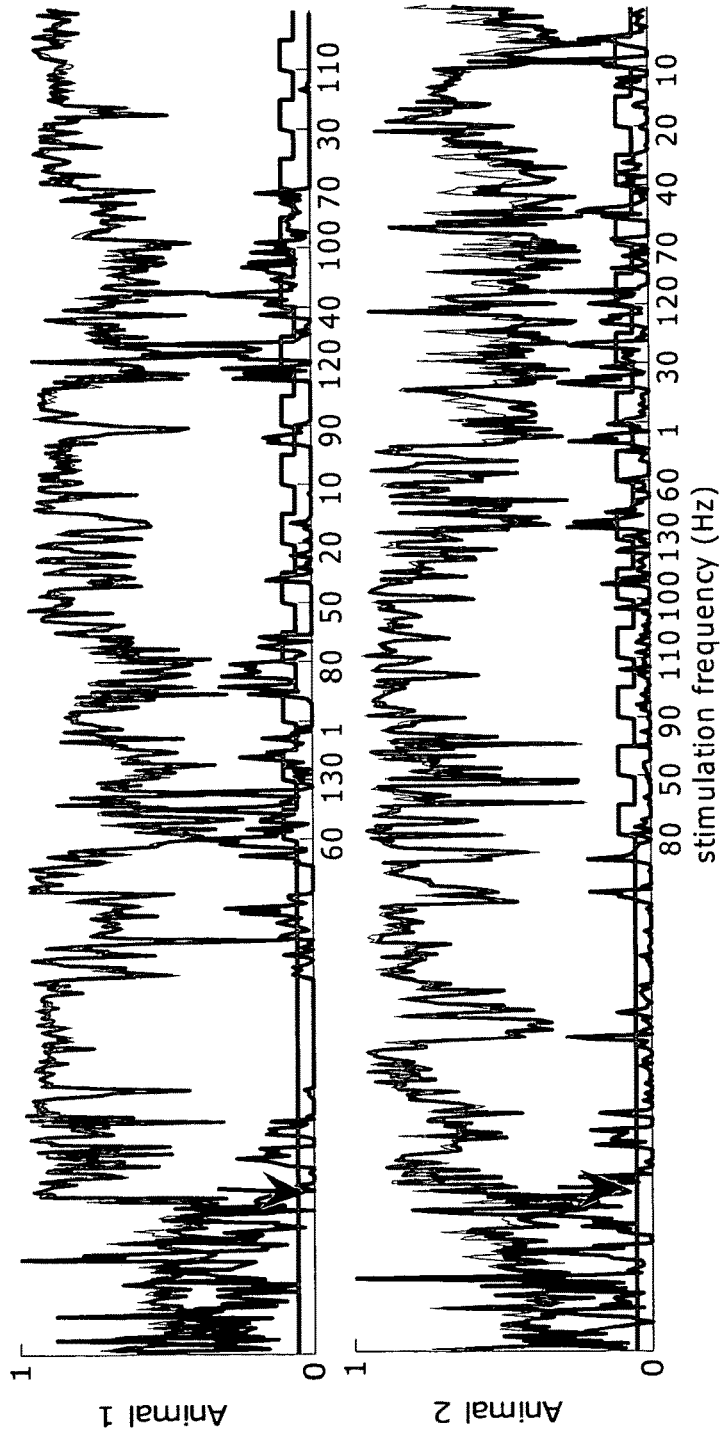

Figure 7. Effect of infraorbital stimulation on spectral index and locomotive activity. The spectral index was computed in non overlapping 10-second windows and plotted against time (red and green lines, striatum and motor cortex respectively). In basal condition the index has a value around 0.5, while after AMPT injection (black arrow) it tends to 1. The application of IS at certain frequencies can bring back the index to basal values, for example at 60 and 120 Hz in Animal 1 (upper panel), and at 130 Hz in Animal 2 (lower panel). Concomitantly, locomotive activity (gray line) is increased during these episodes. Although there is a decrease of the spectral index and an increase of locomotive activity in some of the rest periods, this can be attributed to a residual effect of the immediate previous stimulation.

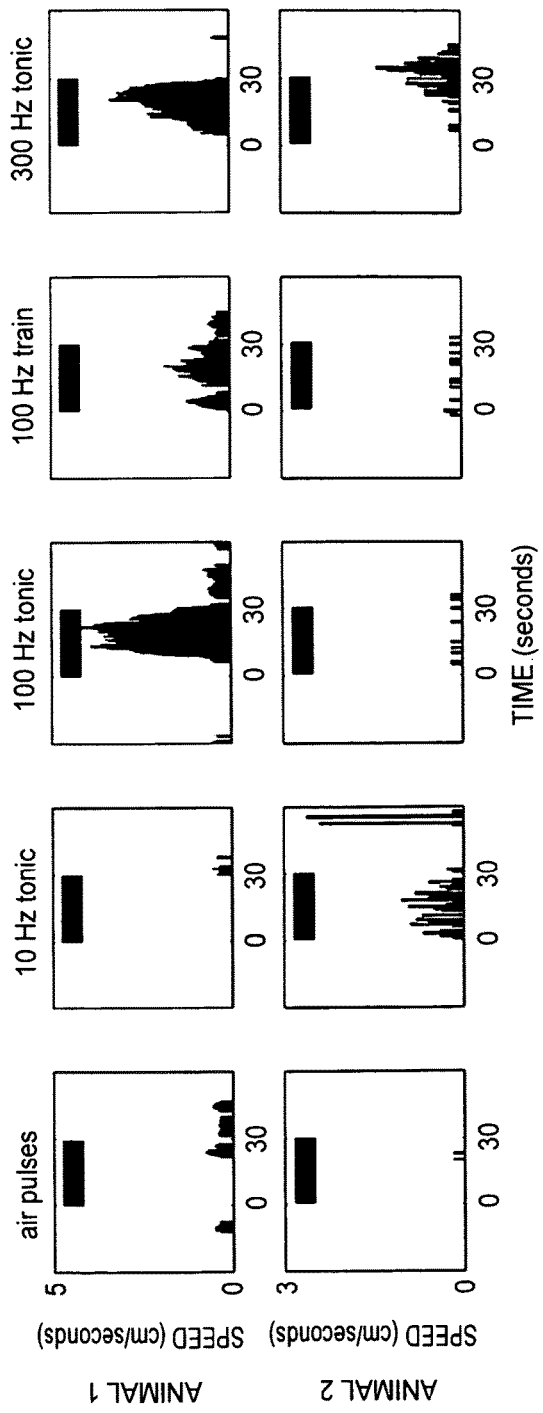

Figure 8. Electrical stimulation of posterior funiculi induces locomotive activity in dopamine depleted mice. Animals were subjected to 4-7 cycles of 5 different stimulation paradigms. Each stimulation epoch lasted 30 seconds. Top row shows the average locomotive activity for 7 cycles for a single animal. Bottom row shows the average results for 5 repetitions for another animal. The paradigm itself is indicated in the top of each plot. The black bar in every plot indicates the stimulation period. The air pulse paradigm was used as a control; it consisted of eight air pulses delivered regularly during 30 seconds and aimed directly at the animal in order to produce non specific stimulation and arousal. Tonic stimulation consists of pulses at the indicated frequency delivered in a continuous way, while train indicates the delivery of a train of 20 pulses at 100 Hz every 2 seconds. Electrical stimulation at 100 Hz, 100 Hz train, and 300 Hz is extremely effective for inducing locomotion in Animal 1; in Animal 2, stimulation at 10 Hz and 300 Hz induces moderate locomotion.

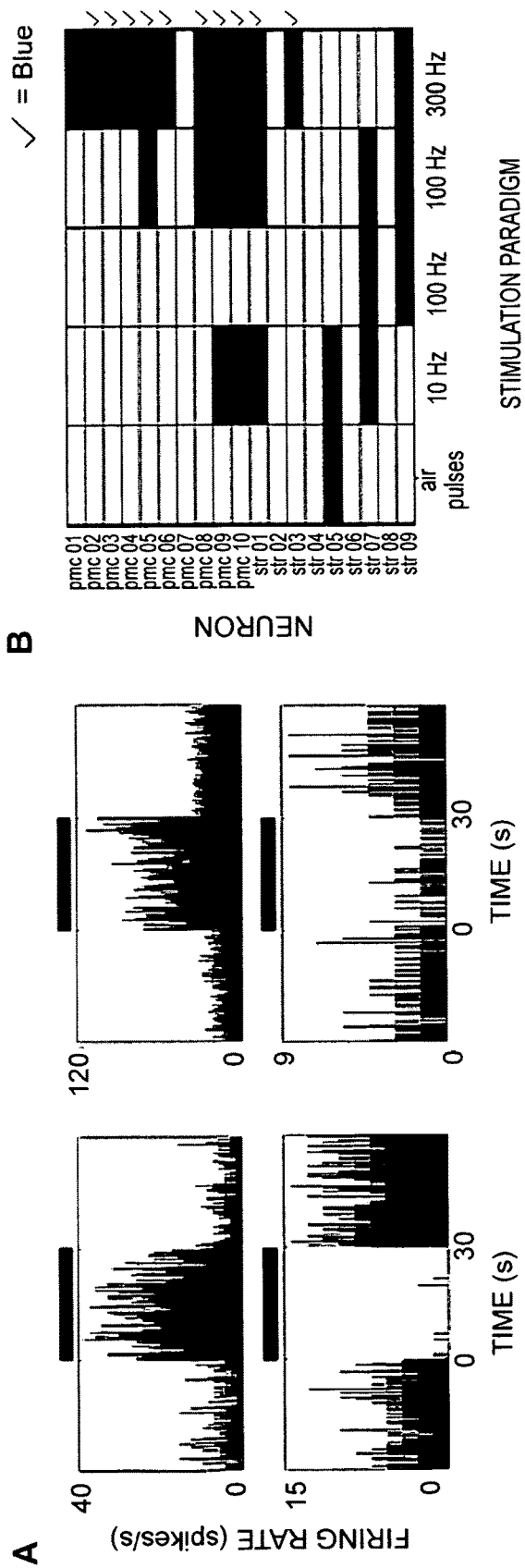

Figure 9. Electrical stimulation of posterior funiculi changes the firing rate of motor cortex and striatal neurons. (A) Average firing rate of example neurons across 7 periods of stimulation at 300 Hz. Black bars indicate stimulation period. Top row, shows a motor cortex neuron (left) and a striatal neuron (right) that exhibit a dramatic increase in firing rate during stimulation. Bottom row shows a motor cortex neuron (left) and a striatal neuron (right) that decrease their firing rates during 300 Hz stimulation. Panel B shows a response matrix for 10 M1 neurons and 9 STR neurons recorded in Animal 1. Each row represents the response of a neuron to 6 stimulation paradigms (columns). Red compartments specify a significant increase in firing rate, while blue compartments point to a significant decrease in firing rate ($p < 0.01$, paired T-test).

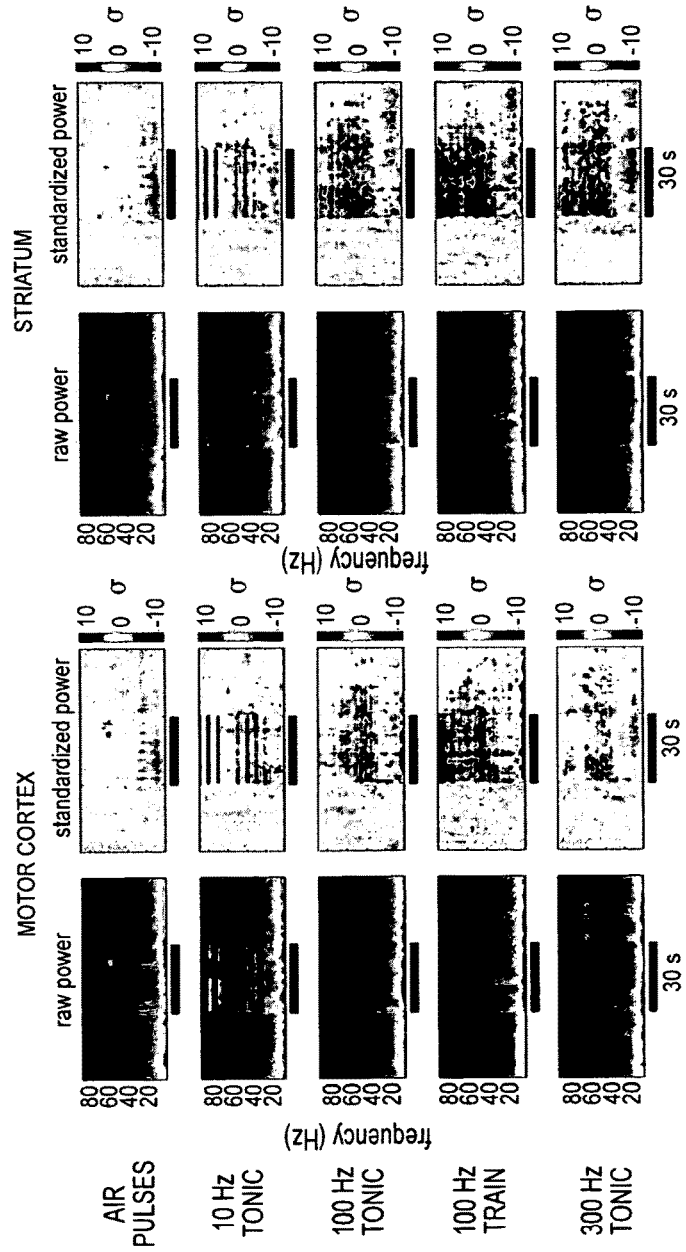

Figure 10. Electrical stimulation of posterior funiculi modifies the temporal activity patterns of neuronal populations in motor cortex and striatum. Average time-frequency charts from 7 recording sites in M1 and 8 recording sites in STR, across 7 stimulation cycles is shown (first and third columns). The abscissa corresponds to time (black bar indicates stimulation period), the ordinate axis corresponds to frequency of oscillatory activity, while the color code indicates the amplitude or power of the oscillations. Warmer colors indicate higher power at that particular time and frequency. In order to detect significant changes in oscillatory power, the data were expressed in terms of standard deviations (σ) from the 30 seconds previous to stimulation for every frequency band (standardized power). Thus, highly significant increases in power will appear red, while significant decrease in power will appear blue. While all the stimulus paradigms, including air pulses, induce a decrease in low frequency power (<20 Hz), only electrical stimulation at 100 Hz tonic, 100 Hz train and 300 Hz clearly increases gamma (30-90 Hz) oscillatory power, a prominent neural feature correlated to motor activity. The horizontal bands observed in the 10 Hz paradigm correspond to electrical artifacts of stimulation.

Tissue content analysis confirms that acute pharmacological dopamine depletion in wild-type mice leads to striatal dopamine levels similar to those observed in PD patients Acute pharmacological dopamine depletion causes parkinsonian like tremor.

Summary of experimental protocol for DCS evaluation in acutely dopamine-depleted wild-type mice.

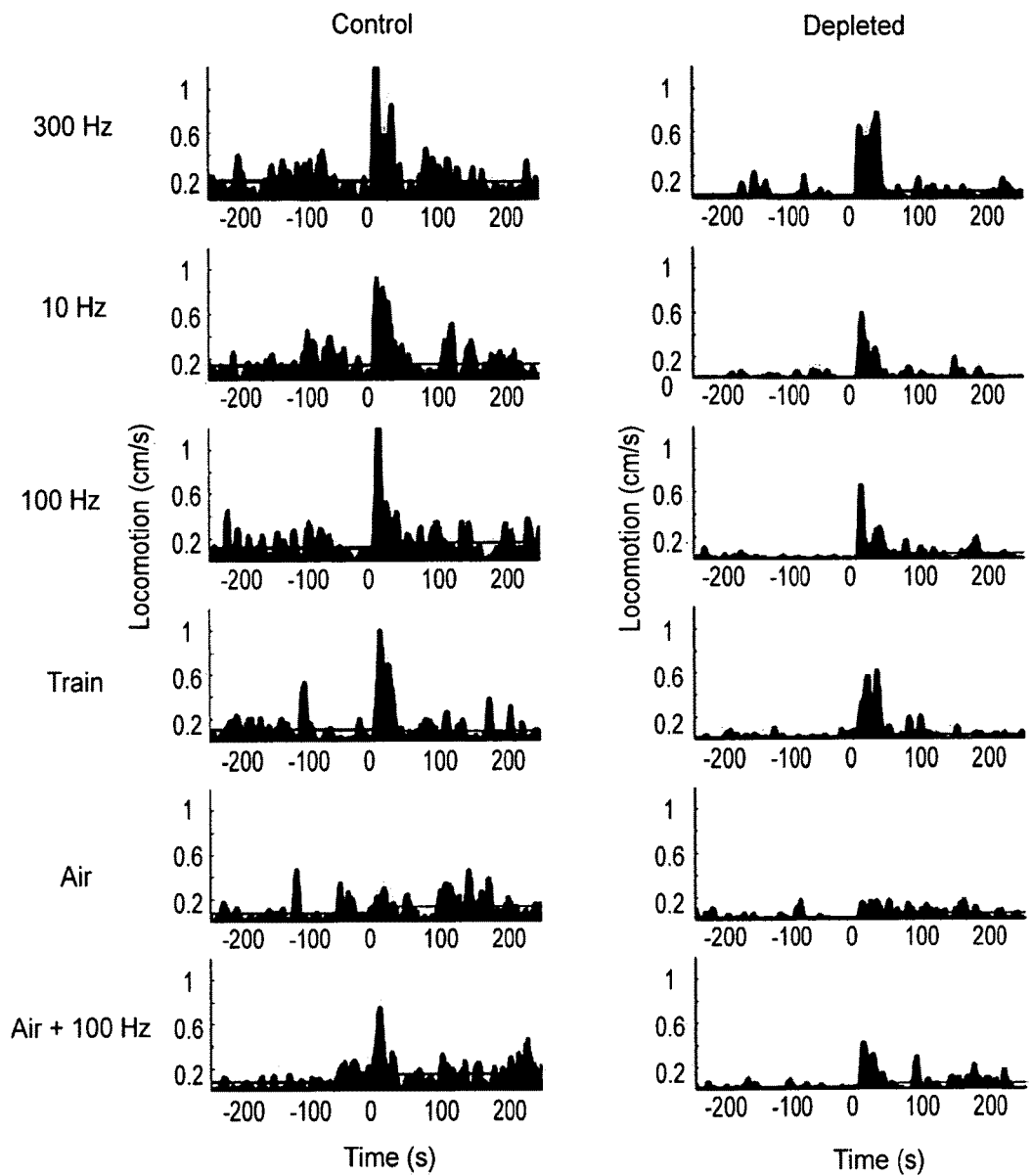

Summary of locomotion induced using different stimulation paradigms.

Average locomotion scored per second in response to the different stimulation paradigms used (30 cycles per paradigm in 9 animals). In spite of the akinesia and bradykinesia displayed in the depleted state, these animals moved almost as far as control animals during stimulation periods using dorsal column stimulation. Yellow bar denotes the extent of stimulation period and black line is the mean activity during a 240s-period before and after stimulation onset.

Figure 15

Spectral composition and neuronal entrainment to striatal local field potentials in depleted and non-depleted states

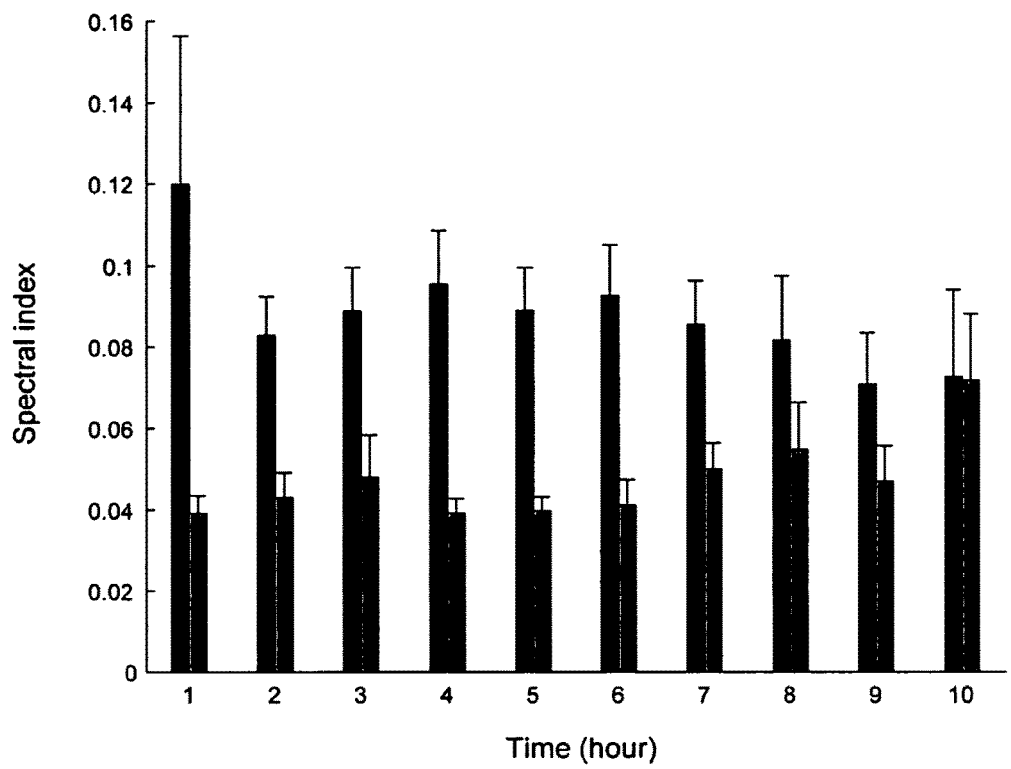

Local field potentials are shifted to higher frequencies as a result of DCS even in severely dopamine depleted animals.

Average spectral indices (power ratio: [25-55]/[1.5-25] Hz) calculated for DCS+L-DOPA (black) and L-DOPA (grey) treated animals, respectively. DCS induced spectral changes even at the lowest L-DOPA dose tested (a single 1mg/kg injection) while the spectral change in the L-DOPA only group occurred during the last hours of the testing period (after more than 20 mg/kg L-DOPA in total) coinciding with onset of locomotion.

Figure 20

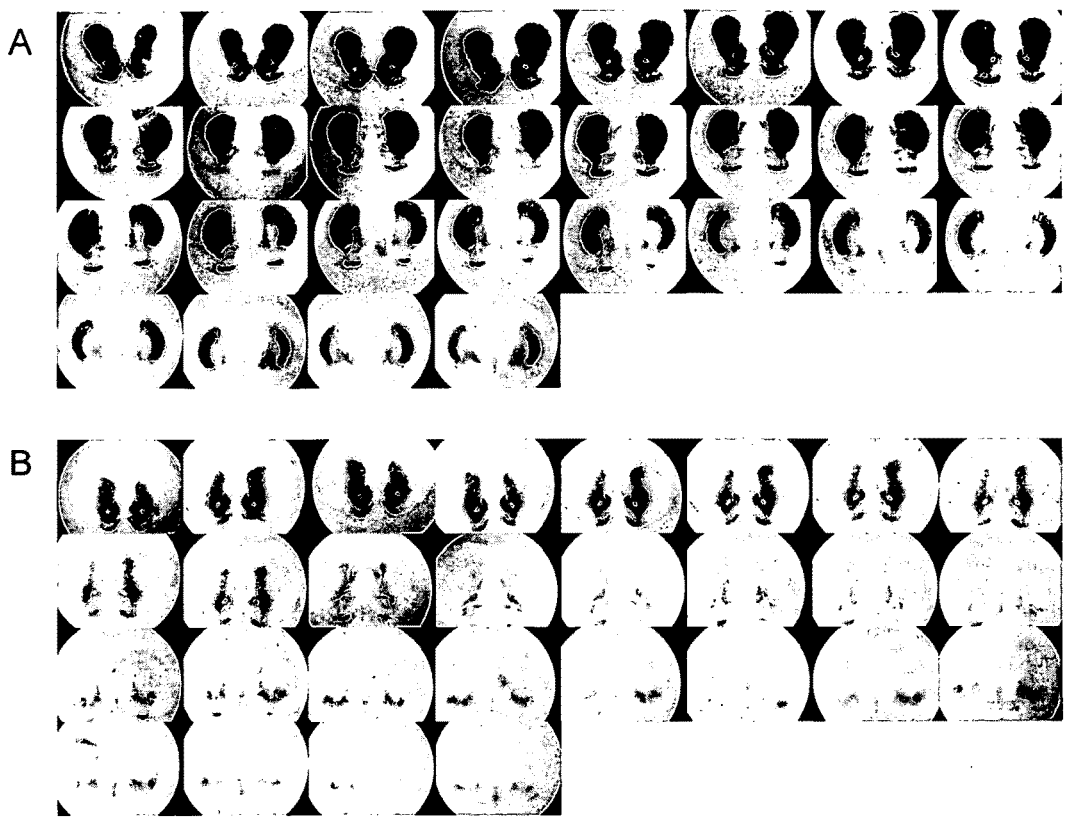

Denervation of dopaminergic input to the striatum in 6-OHDA lesioned rats confirmed by immunohistochemistry for the enzyme tyrosine hydroxylase

Top: coronal sections from a vehicle (0.05% ascorbate saline) injected rat. Bottom: coronal sections from a rat injected with 6-OHDA in three different sites on each side (7 μg per site, 3.5 mg/ml). The panels include sections from ~2 mm anterior to ~2 mm posterior of Bregma (spacing between consecutive sections presented is 80 μm and slice thickness is 40 μm). Quantitative analysis of tyrosine hydroxylase staining in the sections shown indicated a reduction to 21% in 6-OHDA lesioned animals compared to sham treated controls.

Figure 21

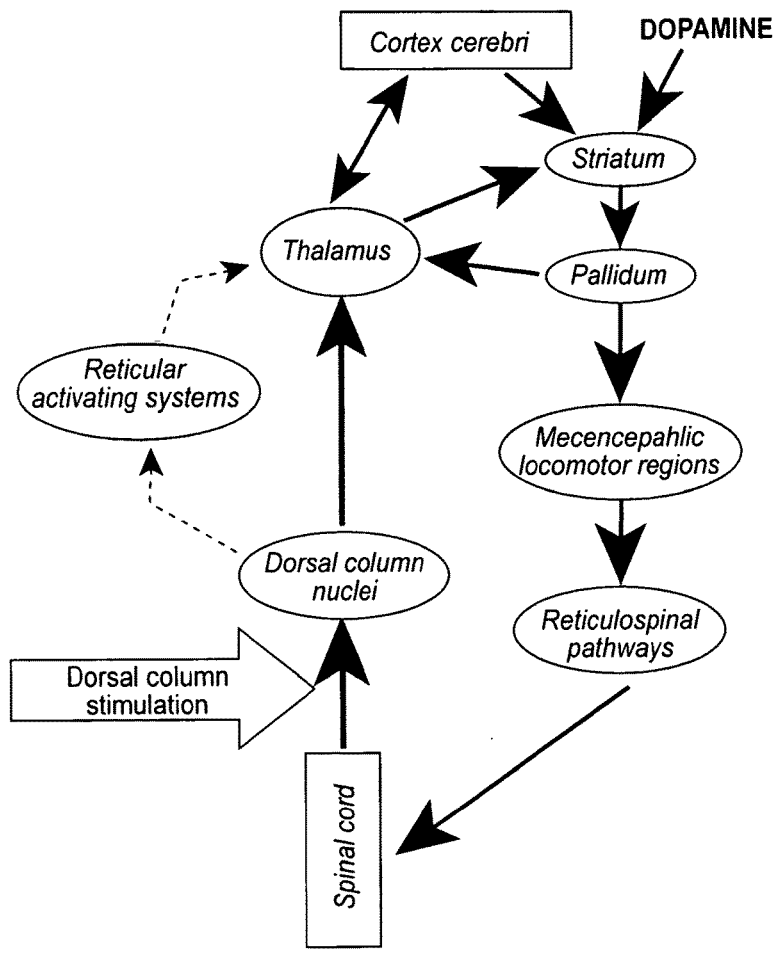

Structures potentially responsible for DCS induced locomotion

DCS is thought to primarily activate ascending primary afferents of the dorsal column pathways terminating in the dorsal column nuclei. The signals may activate various cortical areas either through general arousal systems such as the reticular activating system in the brainstem or by transmission through the leminscal pathway. Both thalamus and cortex exhibit direct excitatory effect on the projecting neurons in the striatum, thereby potentially allowing DCS to modify activity patterns in this cell group. Activity in striatal projection neurons can, in turn, disinhibit motor regions in the brainstem through inactivation of cells in the output nuclei of the basal ganglia (globus pallidus interna, substantia nigra pars reticulate and ventral pallidum) and thereby enable the generation of motor commands to the spinal cord.

Figure 22

METHOD OF TREATING PARKINSON'S DISEASE AND OTHER MOVEMENT DISORDERS

This application is the U.S. national phase of International Application No. PCT/US2008/011219, filed 26 Sep. 2008, which designated the U.S. and claims the benefit to U.S. Provisional Application No. 60/960,356, filed 26 Sep. 2007, the entire contents of each of which are hereby incorporated by reference.

This invention was made with government support under Grant No. 1R21-NS049534 awarded by the National Institutes of Health. The government has certain rights in the invention.

TECHNICAL FIELD

The present invention relates, in general, to movement disorders and, in particular, to methods of treating movement disorders, including Parkinson's Disease.

BACKGROUND

Parkinson's Disease (PD) is one of the most prevalent of the neurodegenerative disorders. PD results from the death of 60-70% of the dopaminergic neurons located in the substantia nigra pars compacta. The motor symptoms of the disease are characterized by bradykinesia or akinesia, rigidity, resting tremors, and gait disturbances (Fahn, Ann. N.Y. Acad. Sci. 991:1-14 (2003)). Currently, dopamine replacement therapy with levodopa is the most widely accepted treatment for PD. Chronic use of the drug, however, leads to long-term complications, such as on-off states and dyskinesia, for about 60% of the patients. Moreover, a large percentage of these patients become unresponsive to the drug, rendering such pharmacological therapy ineffective after a few years.

The most common alternative to dopamine replacement therapy is the direct electrical stimulation of deep brain areas, such as the basal ganglia and thalamus. This therapy is generically known as Deep Brain Stimulation (DBS). In patients with severe PD motor symptoms, chronic continuous high frequency electrical stimulation of motor brain regions, such as the subthalamic nucleus, globus pallidus, or thalamus, can decrease tremors, rigidity, and bradykinesia. DBS also permits the reduction of dopaminergic medication, minimizing the long-term side effects associated with pharmacotherapy.

Unfortunately, DBS requires a stereotactic, high-precision, intracranial surgical procedure, and its efficacy depends on the accuracy of targeting brain nuclei. Additionally, DBS surgery can be associated with serious complications, including intracranial hemorrhage (3.9%) and infections (1.7%). Adverse events related to the device include electrode replacement (4.4%), device dysfunction (3.0%), infection (1.9%) and migration (1.52%) (Kleiner-Fisman et al, Mov. Disord. 21, Suppl 14:S290-S304 (2006)). Thus, despite clear advantages of DBS over L-DOPA therapy, its use is typically restricted to patients in the late stages of PD that are medically stable enough to undergo surgery. That restricts considerably the total number of patients who can benefit from this rather invasive neurosurgical procedure.

The precise neural mechanism by which DBS exerts it effects remains unknown. However, some evidence suggests that its action occurs through the disruption of characteristic aberrant low frequency (<10 Hz) synchronized activity of neuronal populations of basal ganglia and/or motor cortex observed in parkinsonian states (Brown, Mov. Disord. 18:357-363 (2003); Brown et al, Exp. Neurol. 188:480-490 (2004); Costa et al, Neuron. 52:359-369 (2006); Gatev et al, Mov. Disord. 21:1566-1577 (2006)).

The present invention provides new approaches to the utilization of neurostimulation as a continuous therapy for controlling the primary motor symptoms of PD and other movement disorders (e.g. essential tremor (Benabid et al, Lancet 337:403-406 (1991))). The methods to which the invention relates are less invasive than DBS and avoid the complications associated with intracranial surgery.

SUMMARY OF THE INVENTION

The present invention relates generally to methods of treating movement disorders, such as PD, as well as other neurological disorders and certain psychiatric disorders. The methods comprise minimally invasive or non-invasive stimulation of, for example, peripheral cranial nerves or the spinal cord. The methods result in the disruption of the type of pathological synchronous activity observed, for example, in the brains of patients suffering from certain neurodegenerative diseases and disorders, including PD.

Objects and advantages of the present invention will be clear from the description that follows.

BRIEF DESCRIPTION OF THE DRAWINGS

FIGS. 4A-4C. Schematic diagram of an embodiment of a system of the present invention for effecting electrical stimulation of posterior funiculi.

FIG. 5. Single neuron and local field potential activity recorded simultaneously with locomotive activity in a mouse partially depleted of dopamine during bilateral electrical stimulation of the infraorbital nerve. Top: Experiment protocol, a step in the black line indicates infraorbital stimulation (IS) at the specified frequency. Black arrow indicates the α-methyl-p-tyrosine (AMPT) injection. Next 7 panels are the firing rates assessed in 10-second bins for 3 neurons of the dorsolateral striatum (dls-dls3) and 4 neurons of the primary motor cortex (m1-m4). The next 2 panels are spectrograms, representing the oscillatory power of local field potential (a measure of synchronized activity of neural populations) as function of time in the striatum (dis) and primary motor cortex (m). Warm colors represent high power oscillations. Lower panel represents the traveled distance by the mouse in 10-second periods.

FIG. 6. Partial dopamine depletion produces strong synchronization at 4 Hz in the corticostriatal circuit. Blue line is the average power spectra in normal condition; red line is the average power spectra after AMPT injection. Data are from 2 mice (rows). Brain structures indicated on top.

FIG. 7. Effect of infraorbital stimulation on spectral index and locomotive activity. The spectral index was computed in non overlapping 10-second windows and plotted against time (red and green lines, striatum and motor cortex, respectively). In basal condition, the index has a value around 0.5, while after AMPT injection (black arrow) it tends to 1. The application of IS at certain frequencies can bring back the index to basal values, for example, at 60 and 120 Hz in Animal 1 (upper panel), and at 130 Hz in Animal 2 (lower panel). Concomitantly, locomotive activity (gray line) is increased during these episodes. Although there is a decrease of the spectral index and an increase of locomotive activity in some of the rest periods, this can be attributed to a residual effect of the immediate previous stimulation.

FIG. 8. Electrical stimulation of posterior funiculi induces locomotive activity in dopamine depleted mice. Animals were subjected to 4-7 cycles of 5 different stimulation paradigms. Each stimulation epoch lasted 30 seconds. Top row shows the average locomotive activity for 7 cycles for a single animal. Bottom row shows the average results for 5 repetitions for another animal. The paradigm itself is indicated in the top of each plot. The black bar in every plot indicates the stimulation period. The air pulse paradigm was used as a control; it consisted of eight air pulses delivered regularly during 30 seconds and aimed directly at the animal in order to produce non specific stimulation and arousal. Tonic stimulation consists of pulses at the indicated frequency delivered in a continuous way, while train indicates the delivery of a train of 20 pulses at 100 Hz every 2 seconds. Electrical stimulation at 100 Hz, 100 Hz train, and 300 Hz is extremely effective for inducing locomotion in Animal 1; in Animal 2, stimulation at 10 Hz and 300 Hz induces moderate locomotion.

FIGS. 9A and 9B. Electrical stimulation of posterior funiculi changes the firing rate of motor cortex and striatal neurons. (FIG. 9A) Average firing rate of example neurons across 7 periods of stimulation at 300 Hz. Black bars indicate stimulation period. Top row shows a motor cortex neuron (left) and a striatal neuron (right) that exhibit a dramatic increase in firing rate during stimulation. Bottom row shows a motor cortex neuron (left) and a striatal neuron (right) that decrease their firing rates during 300 Hz stimulation. FIG. 9B shows a response matrix for 10 M1 neurons and 9 STR neurons recorded in Animal 1. Each row represents the response of a neuron to 6 stimulation paradigms (columns). Red compartments specify a significant increase in firing rate, while blue compartments point to a significant decrease in firing rate ($p<0.01$, paired T-test).

FIG. 10. Electrical stimulation of posterior funiculi modifies the temporal activity patterns of neuronal populations in motor cortex and striatum. Average time-frequency charts from 7 recording sites in M1 and 8 recording sites in STR, across 7 stimulation cycles is shown (first and third columns). The abscissa corresponds to time (black bar indicates stimulation period), the ordinate axis corresponds to frequency of oscillatory activity, while the color code indicates the amplitude or power of the oscillations. Warmer colors indicate higher power at that particular time and frequency. In order to detect significant changes in oscillatory power, the data were expressed in terms of standard deviations ($\sigma$) from the 30 seconds previous to stimulation for every frequency band (standardized power). Thus, highly significant increases in power will appear red, while significant decreases in power will appear blue. While all the stimulus paradigms, including air pulses, induce a decrease in low frequency power (<20 Hz), only electrical stimulation at 100 Hz tonic, 100 Hz train and 300 Hz clearly increases gamma (30-90 Hz) oscillatory power, a prominent neural feature correlated to motor activity. The horizontal bands observed in the 10 Hz paradigm correspond to electrical artifacts of stimulation.

FIG. 12A. Examples of 5 min EMG recordings from nuchal muscles during rest from a depleted animal (red) and a control animal (green; rectified voltage was summed in 100 ms time bins). Note the periodic bursts in the dopamine depleted state in contrast to the almost atonic state in control conditions. FIG. 12B. Auto-correlogram of time bins (shown in a) with an amplitude greater than twice the mean. Bursts tended to occur with a ~3 s period, although this interval varied slightly over time and between animals. FIG. 12C. High-frequency components within bursts. Examples of frequency spectrums from nuchal muscles in a WT mouse during two 30 min recordings before (green) and after (red) dopamine depletion; several differences in the distribution of spectral power is discernable, e.g. the peaks at ~16.5 Hz and 25 Hz with higher harmonics. Inset shows temporal appearance of the bursts.

FIG. 13A. The average amount of locomotion displayed per second in the open-field is significantly reduced after acute pharmacological dopamine depletion in wild-type mice (mean and SEM shown, $p<0.001$, Mann-Whitney). FIG. 13B. A preferential reduction of faster movements reflects the bradykinesia in the depleted state; number of events expressed as percentage of non-depleted values for the three intervals are shown. FIG. 13C. Examples of local field potential (LFP) spectrograms and firing rate plots recorded in MI during two 5-minute periods in the same animal, before and after dopamine depletion. Top row: locomotion during recording periods, second row: LFP power, third row: LFP power standardized to the non-depleted 5-minute period. Note the increased power in low frequencies in the depleted state (*) and the normalization of spectral power upon locomotion (red arrow). Bottom row: average firing per second for 6 MI units. FIG. 13D. Set-up for electrical stimulation of dorsal columns: The stimulation electrode (red) is implanted above the dorsal spinal cord and connection wires are passed subcutaneously to a special connector attached to the skull. Two stimulus-isolator units provide biphasic constant-current pulses at desired frequency and intensity. FIG. 13E. Schematic dorsal (left) and sagittal view (right) of the implanted electrode. r: rostral; c: caudal.

injections, 2 h apart. When the animal displayed clear catalepsy acquisition of data related to the depleted state was initiated.

FIG. 15. Summary of locomotion induced using different stimulation paradigms. Average locomotion scored per second in response to the different stimulation paradigms used (30 cycles per paradigm in 9 animals). In spite of the akinesia and bradykinesia displayed in the depleted state, these animals moved almost as far as control animals during stimulation periods using dorsal column stimulation. Yellow bar denotes the extent of stimulation period and black line is the mean activity during a 240 s-period before and after stimulation onset.

Figure 16:
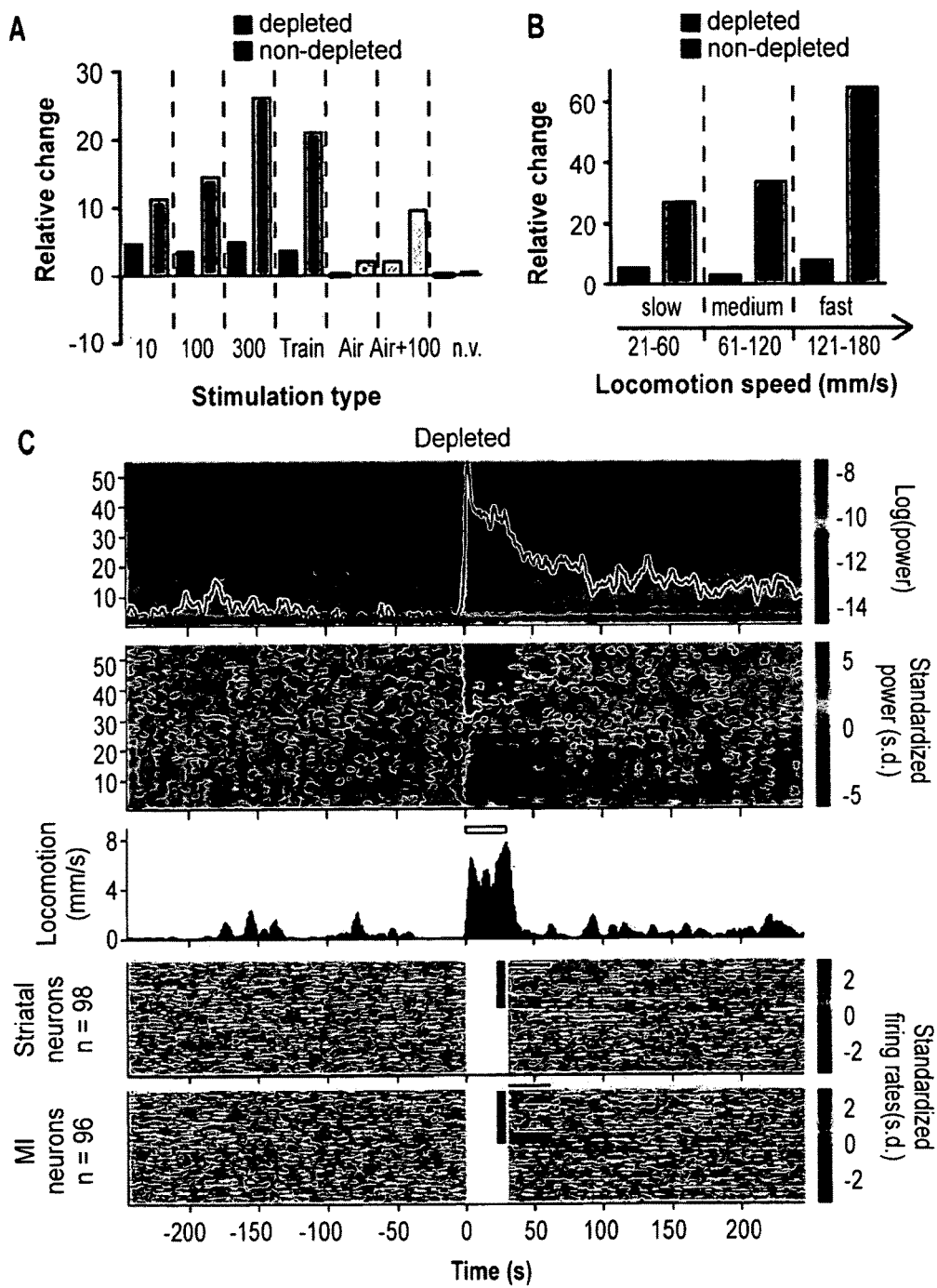

FIGS. 16A-16C. DCS restores locomotion and desynchronizes corticostriatal activity. FIG. 16A. Relative change in amount of locomotion in depleted and non-depleted mice (DCS frequencies specified on x-axis, n.V: trigeminal nerve stimulation; mean and SD shown, means for all conditions before and after depletion are significantly different, $\alpha=0.005$). FIG. 16B. DCS preferentially increases the fraction of fast movement components in dopamine depleted animals but not in controls. FIG. 16C. Average spectrograms of striatal LFPs and firing rates recorded around twenty-one 300 Hz stimulation events (yellow bar), top row: LFP power (black trace denotes spectral index, see main text) second row: LFP power standardized to first 240 s. Standardized firing rate to first 240 s of 98 striatal and 96 cortical units (row 4 and 5, respectively; firing rate during stimulation period was omitted because of potential artefacts). Neurons exhibiting significant changes during the 30 s-period following stimulation (black line) are indicated with red and blue rectangles (excitatory and inhibitory responses). Middle row: Average locomotion (n=36 events).

FIGS. 17A-17D. Spectral composition and neuronal entrainment to striatal local field potentials in depleted and non-depleted states. FIG. 17A. Example of power spectral densities for a single animal (mean and standard deviation of 375 non-overlapping 4-second periods (in total 25 min). Depleted condition (red) showed stronger oscillations around 1.5-4 Hz and in the lower beta range (10-15 Hz), whereas the power of oscillations >25 Hz was decreased in relation to non-depleted condition (green). FIG. 17B. Spectral power (median±median absolute deviation) of striatal LFP oscillations from 9 animals in control and depleted state (25 m-periods). Significant differences were found for all studied frequency ranges (***, $\alpha=0.001$; Mann-Whitney test). FIG. 17C. Example of a striatal unit entrained to the LFP recorded in the same brain structure during dopamine-depletion. Top row shows the STA LFP during control and dopamine-depleted states. Bottom row shows the power spectra calculated from the STA (black trace), while dashed red line denotes significance level ($\alpha=0.001$) for the spectral power values. FIG. 17D. Preferred STA power of 85 striatal neurons in control (green) and dopamine-depleted (red) state from 9 animals (median±median absolute deviation).

Figure 18:
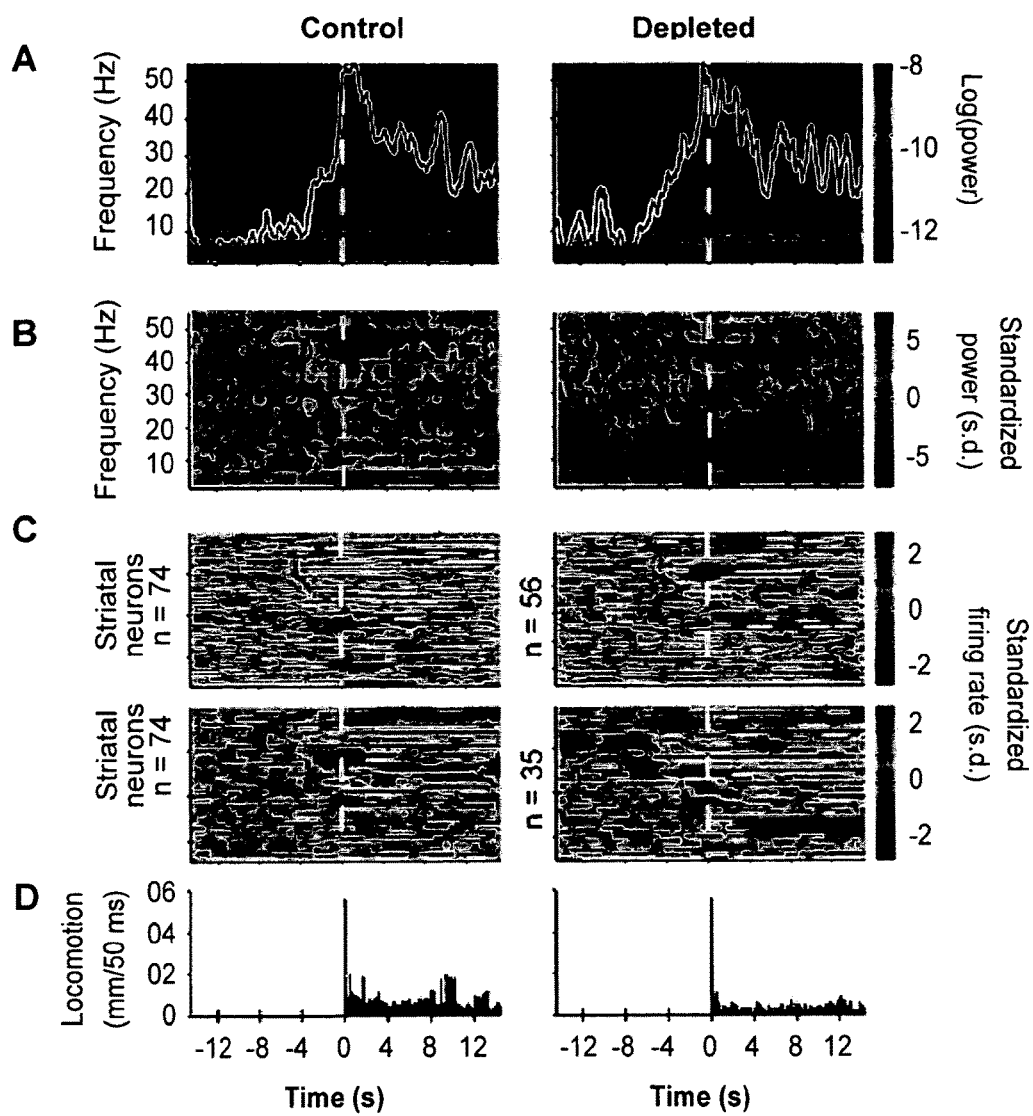

FIGS. 18A-18D. Activity patterns during spontaneous locomotion. FIG. 18A. Average spectrogram (window of 1.024 s, slid every 0.5 s) of striatal LFP aligned to the onset of spontaneous locomotion in control condition (n=115 events) and dopamine-depleted condition (n=51 events). The gradual shift from lower to higher frequencies indicated by the average spectral index (black trace) starts before locomotion onset (dashed white line). FIG. 18B. Standardization of spectrogram relative to preceding non-locomotion periods (average spectrogram of 112 stationary 10 s-duration events). FIG. 18C. Firing rate (binned at 0.5 s) of striatal and MI units around the onset of spontaneous locomotion. Significant changes in firing rate (as compared to stationary period) are indicated with magenta crosses (excitatory) and dark blue crosses (inhibitory response). FIG. 18D. Average locomotion during recorded events.

Figure 19:
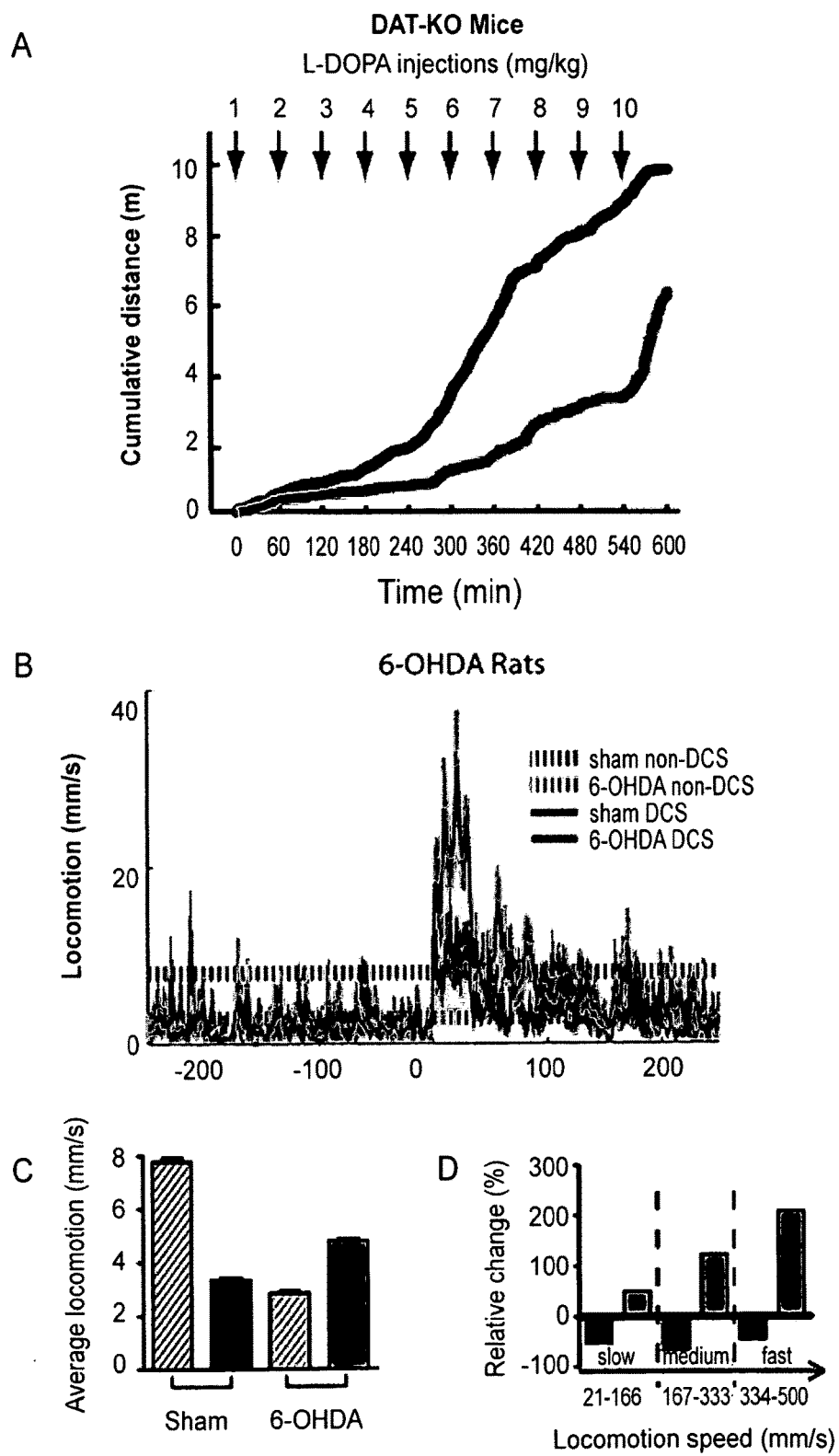

FIGS. 19A-19D. DCS restores locomotion in severely dopamine-depleted mice and in chronically lesioned rats. FIG. 19A. The cumulative amount of locomotion scored in animals receiving DCS in combination with successive L-DOPA injections (black) was significantly higher at all time points than what was observed for the group only receiving L-DOPA (grey). FIG. 19B. DCS (yellow shaded area) induced a prominent increase in average locomotion per second in 6-OHDA lesioned rats (shaded area around trace is SEM). A residual effect of the stimulation can be observed up to 100 s after stimulation is turned off. The average amount of locomotion for the same rats during normal conditions was obtained from non-DCS sessions. In the sham group, in contrast, the average locomotion per second decreased compared to non-DCS sessions (mean±SEM, n=64 stimulation and 64 control sessions for both sham treated and lesioned rats). FIG. 19C. DCS specifically increases locomotion in 6-OHDA lesioned rats (mean and SEM shown; all means are significantly different to the others, p<0.001, Kruskal-Wallis and Dunn's multiple comparison test; flashes indicate DCS sessions). FIG. 19D. A preferential relative increase of fast locomotion episodes was found in the 6-OHDA lesioned group reflecting alleviation of bradykinetic symptoms. Ratios of the sum of recorded locomotion episodes in three speed intervals [DCS/non-DCS sessions] are shown (blue: sham, red: 6-OHDA).

FIG. 20. Local field potentials are shifted to higher frequencies as a result of DCS even in severely dopamine depleted animals. Average spectral indices (power ratio: [25-55]/[1.5-25] Hz) calculated for DCS+L-DOPA (black) and L-DOPA (grey) treated animals, respectively. DCS induced spectral changes even at the lowest L-DOPA dose tested (a single 1 mg/kg injection) while the spectral change in the L-DOPA only group occurred during the last hours of the testing period (after more than 20 mg/kg L-DOPA in total) coinciding with onset of locomotion.

FIGS. 21A and 21B. Denervation of dopaminergic input to the striatum in 6-OHDA lesioned rats confirmed by immunohistochemistry for the enzyme tyrosine hydroxylase. FIG. 21A: coronal sections from a vehicle (0.05% ascorbate saline) injected rat. FIG. 21B: coronal sections from a rat injected with 6-OHDA in three different sites on each side (7 μg per site, 3.5 mg/ml). The panels include sections from ~2 mm anterior to ~2 mm posterior of Bregma (spacing between consecutive sections presented is 80 μm and slice thickness is 40 μm). Quantitative analysis of tyrosine hydroxylase staining in the sections shown indicated a reduction to 21% in 6-OHDA lesioned animals compared to sham treated controls.

FIG. 22. Structures potentially responsible for DCS induced locomotion. DCS is thought to primarily activate ascending primary afferents of the dorsal column pathways terminating in the dorsal column nuclei. The signals may activate various cortical areas either through general arousal systems such as the reticular activating system in the brainstem or by transmission through the leminscal pathway. Both thalamus and cortex exhibit direct excitatory effect on the projecting neurons in the striatum, thereby potentially allowing DCS to modify activity patterns in this cell group. Activity in striatal projection neurons can, in turn, disinhibit motor regions in the brainstem through inactivation of cells in the output nuclei of the basal ganglia (globus pallidus interna, substantia nigra pars reticulate and ventral pallidum) and thereby enable the generation of motor commands to the spinal cord.

DETAILED DESCRIPTION OF THE INVENTION

The present invention relates to neurostimulation methods for disrupting the pathological synchronous activity observed in the brains of patients suffering from certain movement or motor diseases/disorders, including, but not limited to, PD, cortical or subcortical stroke, amyotrophic lateral sclerosis, essential tremor, Creutzfeldt-Jakob disease, multiple sclerosis, ataxia or other cerebellar disorder, as well as dystonia or dyskinesia. The present methods can also be used in the treatment of patients suffering from other neurological disorders or from certain psychiatric disorders (e.g., patients suffering from various types of epilepsy, depression or obsessive compulsive disorder). In contrast to DBS, these methods involve either minimally invasive or non-invasive stimulation (e.g., electrical stimulation) of peripheral cranial nerves, such as the trigeminal and vagus nerves (advantageously, uni- or bilateral stimulation of the maxillary branch of the trigeminal nerve (or the vagal nerve unilaterally)), the dorsal sensory roots of spinal nerves, or the posterior funiculus of the spinal cord that form the ascending fibers of the medial lemniscus-dorsal column pathway of the somatosensory system. The advantages of using peripheral nerves (or the spinal cord) as the focus of the stimulation protocol are significant. In addition to requiring minimal or no surgical intervention to apply an electrode to these nerves and neural pathways, this approach also has the advantage that many more stimulation protocols can be tested in each patient in order to determine the optimum protocol. Further, reduced power requirements suitable for use in these approaches eliminate the need for subcutaneous implantation of large batteries. In addition, this paradigm reduces to zero the risk of brain hemorrhage (the main and most serious side effect of DBS), greatly minimizes or totally eliminates the risk of brain infection, and reduces significantly the likelihood of rejection of chronically implanted foreign materials. These advantages increase many fold the total number of patients who can benefit from neurostimulation therapy alone or in combination with other therapeutic strategies (e.g., dopamine replacement in the case of PD patients), while significantly reducing the associated morbidity.

In accordance with the present invention, chronically implanted peripheral nerve cuff electrodes, stimulators of the posterior funiculi, or electrical stimulators applied to the skin surface are employed to generate an essentially innocuous electrical stimulation that disrupts synchronous neural activity in higher brain centers, such as the motor cortex and the basal ganglia. Disruption of this synchronous neural activity, which precludes initiation of voluntary movements (akinesia), provides continuous relief of the symptoms experienced by patients (human or non-human animal patients) with movement diseases/disorders, for example PD, or other neurological disorders or certain psychiatric disorders.

Figure 1:
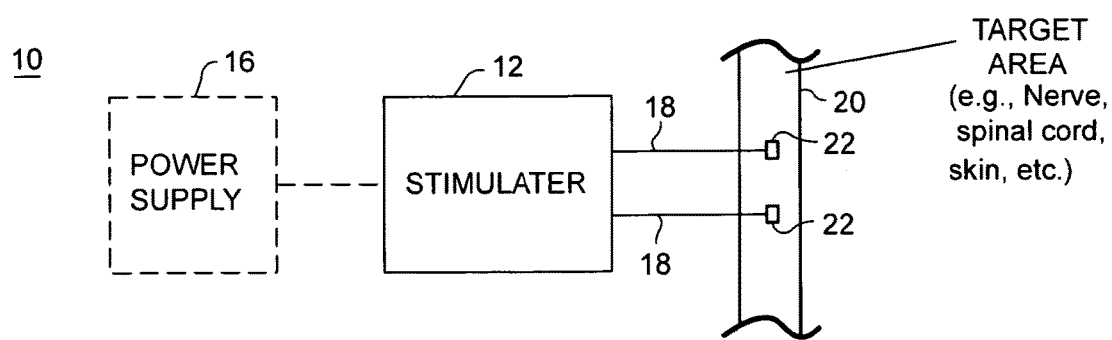
FIG. 1. Schematic diagram illustrating a non-limiting example stimulation system.

FIG. 1 illustrates a non-limiting example stimulation system 10. A stimulator 12 generates a stimulating signal that is delivered to a target area 20 of a patient through suitable conductors 18 and contact points 22. The area 20 corresponds to or is proximate to one or more motor-related nerves or neural pathways. Non-limiting examples of such areas include infraorbital nerves, posterior funiculi of the spinal cord, and epidurally above the nerve or neural pathway to be stimulated.

The stimulator 12 can generate an electrical, optical, or any other suitable type of stimulating signal. In a preferred, non-limiting implementation, the stimulator 12 generates and delivers an electrical stimulation signal. In that case, the conductors 18 are electrical conductors and the contact points 22 are electrically conductive contact points. Preferably, the stimulator 12 is a small electronic circuit that can be implanted under the skin of, or disposed outside the body of, the patient.

Non-limiting examples of commercially available electrical stimulators suitable for use in the invention include the electrical Muscle Stimulator EMS 400 available from ReliaMed, Brooklyn Park, Minn. The stimulator 12 can be powered by an integrated power supply or by a separate power supply 16, the latter being illustrated with dashed lines. One example power supply is a battery and small sized batteries such as lithium batteries may be desirable for human applications. Although not required, it is preferred that the stimulator 12 be programmable in order to set or vary (or later adjust) one or more various stimulation parameters such as, for example, signal amplitude, frequency, pulse width, pulse asymmetry, polarity, etc.

The objective of the stimulator 12 is to deliver a signal that disrupts aberrant low frequency synchronization in motor related neural circuits to facilitate volitional movement. In this case, synchronization means the coordinated activity of the neural circuit at a low frequency, e.g., less than 10 Hz. The stimulator 12 disrupts that low frequency synchronization and consequently the overall activity of the neural circuits resembles normal activity patterns which are characterized by a higher frequency range, e.g. over 30 Hz. Examples of an electrical stimulating signal include electrical pulses emitted at a frequency of 100 and 300 Hz applied continuously or in short periods (trains). Pulse durations can vary. Excellent results have been obtained using biphasic pulses having pulse durations between 250 μsec to 1 msec. Biphasic pulses can vary between themselves in amplitude and duration. The range of amplitude or intensity of the stimulating signal depends on the patient and the effect sought.

Figure 2:
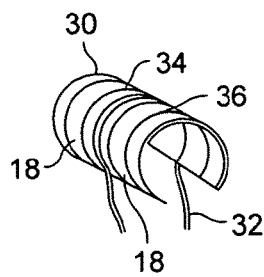
FIG. 2. Illustration of a non-limiting example wherein electrical stimulation is delivered to a nerve using a cuff structure.

There are different ways that the stimulating energy can be delivered to the area to be simulated. FIG. 2 illustrates a non-limiting example wherein electrical stimulation is delivered to a nerve using a cuff structure 30. The cuff can be place around a nerve, for example, and secured using a tie material 32 which can be silk or other suitable material. Other securing mechanism, such as adhesive, clamp, etc., can be used. The cuff includes two separated conductive bands 34 and 36, each coupled to one of the conductors 18. The bands can, for example, be made of platinum but other suitable conductive materials can be used. The conductors 18 that connect the bands to the stimulator 12 can be insulated with suitable material. The two bands 34 and 36 are spaced to permit current flow and to deliver an optimal current density profile for stimulating the area 20.

Figure 3:
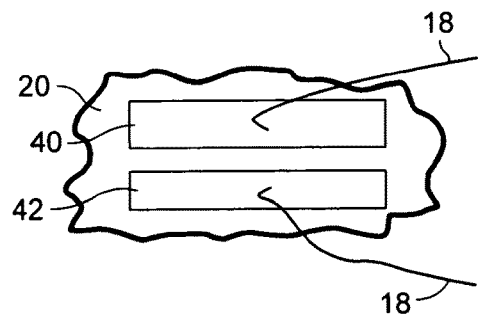
FIG. 3. Illustration of a non-limiting example wherein electrical stimulation is delivered to a nerve/neural pathway (e.g., spinal cord) using contact electrodes.

Another non-limiting example is shown in FIG. 3 wherein electrical stimulation is delivered to the area 20 (e.g., the spinal cord of a patient) using contact electrodes 40 and 42. In this example, the contact electrodes 40 and 42 are spaced apart rectangles but they can be other shapes of suitable size to deliver the desired stimulation to area 20. As in the example in FIG. 3, the contact electrodes 40 and 42 can be made of platinum and connected to the stimulator 12 via insulated wire conductors.

In one embodiment of the invention, a stimulatory system as described above is used in stimulating an infraorbital nerve. In accordance with this embodiment, a nerve contact electrode, which is preferably a nerve cuff electrode, is in contact with the nerve to be stimulated. The electrode is manufactured of a conductive material so as to transmit an electrical pulse. Additionally, the electrode is preferably treated to minimize any potential physiological reaction to the electrode, and to insulate the portion or portions of the electrode that do not contact the nerve. Suitable insulation materials include, but are not limited to, TEFLON® for a lead wire and SYLGARD® (available from Dow Corning Corp. of Midland, Mich.) for a nerve contact electrode.

As indicated above, the nerve contact electrode is preferably a nerve cuff electrode. A nerve cuff electrode is an electrode designed to encircle the nerve to be stimulated, thereby increasing the area of contact and stimulation. A suitable nerve cuff electrode can comprise one or more conductive bands optionally mounted on a support surface. Preferably, a conductive band comprises platinum. When a plurality of conductive bands are employed in a nerve cuff electrode, it is preferable that the bands be communicatively associated with one another such that when a stimulation pulse is applied to the nerve cuff electrode it is dispersed through all bands of the electrode. Additional wire or other material can be affixed to the nerve cuff electrode in order to permit its emplacement around the nerve to be stimulated. Areas of the electrode through which it is not desired to transmit current can be coated with an insulator.

Leads from each band of the nerve contact electrode are attached to the power source such that current passes from one band to the next. The nerve is activated when current passes from one band to the next.

Nerve cuff electrodes can be implanted by surgically exposing the nerve and orienting the electrodes such that they surround the nerve. Nerve cuff electrodes can be implanted either on only one branch of a nerve, (e.g., the left branch of the infraorbital nerve), or on both branches of the nerve (e.g., the right and left branches of the infraorbital nerve). Implantation of a nerve cuff electrode on a single branch of a nerve present in a subject can facilitate unilateral stimulation of that nerve. However, implantation of a nerve cuff electrode on two or more branches of a nerve present in a subject can facilitate bilateral stimulation of that nerve.

As regards stimulation parameters, values will be limited by the technical specifications of the stimulator:

Electrode polarity: electrode polarity (when one of the two electrodes is positive or negative) is not necessarily relevant for the achievement of beneficial effects. In the case of trigeminal (infraorbital or supraorbital) stimulation, bilateral implantation is preferred, since it is more effective than unilateral implantation (Fanselow et al, J. Neurosci. 20:8160-8168 (2000)). In the case of PD it can be important to use bilateral stimulation to conserve the symmetry of the stimulation and produce a comparable effect in both hemispheres of the brain.

Pulse duration: exemplary values are 250 µs, 500 µs and 1 ms. The longer the pulse duration, the less the current intensity needed to achieve desired effect.

Frequency: for example, 100 Hz up to 300 Hz.

Current intensity: this is a critical parameter to be controlled. Intensity is adjusted for every frequency and pulse duration configuration, advantageously, starting with the minimum intensity available with the stimulator used. The intensity reported as comfortable for trigeminal nerve transcutaneous stimulation in humans is <20 mA (DeGiorgio et al, Epilepsia 47:1213-1215 (2006)).

The optimization of these parameters can be carried out in a manner similar to the programming of DBS in PD patients (Volkmann et al, Mov. Disord. 21 Suppl 14:S284-289 (2006)), which can be described briefly as follows. Predetermined values for electrode polarity, pulse duration and frequency are selected, while intensity is set at the minimum possible. The stimulation is turned on and evaluation of beneficial effect and side effects are performed. This step is repeated while increasing current intensity in small increments. Rigidity is a key aspect for evaluating beneficial effects, since, in DBS, it responds usually within seconds. Alleviation of bradykinesia and tremor may exhibit variable delay. Motor tasks described in items 23-29 of the Unified Parkinson's disease Rating Scale can also be used. Side effects include the perception of tingling, pain and ultimately, muscle contraction. The last two of these side effects are preferably avoided.

The same general strategy can be used to stimulate the dorsal roots or the sensory branches of spinal nerves in order to obtain a similar motor effect. FIG. 3 is a schematic of a further embodiment of the invention, that is, a system for effecting electrical stimulation of posterior funiculi (see also FIG. 4). Direct electrical stimulation of the dorsal columns of the posterior funiculus of the spinal cord, the region containing the ascending fibers of the dorsal-column medial lemniscus pathway, can be used to generate the same motor effects in patients (e.g., PD patients), that is, increase in locomotion activity and block of peripheral tremor. Posterior funiculi, also known as dorsal columns, convey tactile and proprioceptive input to supraspinal structures. As shown in Example 2, electrical stimulation of the posterior funiculi can alleviate akinesia in a pharmacological PD model. Consistently, stimulation of the posterior funiculi is also associated with electrophysiological activity patterns similar to those displayed during normal motor activity (see Example 3 below).

Preferred parameters for effecting electrical stimulation of the posterior funiculi are as follows. Electrical stimulation can consist of biphasic squared constant current pulses of 2 ms duration delivered at different frequencies. Four stimulation paradigms have been tested in animals: 10 Hz, 100 Hz, 300 Hz and 0.5 Hz trains each consisting of 20 pulses at 100 Hz. In animal studies, the current intensity can be adjusted based on the behavioral response of the animal. Threshold intensity for each paradigm can be established as the minimum current at which a clear associated behavior, such as transient freezing, arousal, or uneasiness, is displayed. For the study described in the Example 2 that follows, 1.2-1.5 fold the threshold was used, which corresponds to 180-450 microamperes.

Posterior funiculi stimulation (PFS). PFS can be achieved by chronic implantation of, for example, custom made platinum flat-electrodes (FIG. 4A) positioned epidurally above the posterior funiculi of the spinal cord (FIGS. 4B and 4C) at the upper thoracic level. Bilateral stimulation of the cord is preferred.

In addition to the techniques described above for trigeminal and spinal cord stimulation, which are invasive, other non-invasive approaches can be used to stimulate the trigeminal nerve. For example, transcutaneous trigeminal nerve electrical stimulation can be used. This method is non-invasive and fully reversible, allowing for testing effectiveness and tolerability. Commercially available surface electrical stimulators can be employed in the practice of this invention. A surface stimulator can be positioned on the surface of the face, for example, on top of the trigeminal nerve. Electrical current delivered by a skin surface stimulator can be expected to produce the same type of effect observed with nerve cuff electrodes. For example, electrical muscle stimulator EMS 400 (ReliaMed, Brooklyn Park, Minn.) can be employed which provides biphasic asymmetrical pulses of 250 μs duration at a maximum of 120 Hz. The intensity range is 0-100 mA. Dimensions are 27×62×95 mm, and weight is 140 g including the batteries (see www.vitalityweb.com/backstore/ems.htm). Silver-gel auto-adhesive stimulation electrodes can also be used (Superior Silver-Permagel Electrodes, Tyco Healthcare/Uni-Patch, Wabasha, Minn., U.S.A.), and a 9 V DC battery. In accordance with this embodiment, all components, including the electrodes, can be disposed outside the body of the patient. The auto-adhesive electrodes can be attached to the skin while the EMS unit can be carried in a belt or bag.

Percutaneous nerve stimulation electrodes can also be used to effect non-invasive stimulation. In accordance with this approach, part or all of the stimulation setup is implanted in the patient's body. Self-sizing cuff electrodes suitable for trigeminal stimulation (infraorbital nerve or supraorbital nerve) can be used that are commercially available from Neurotech (Louvain-la-Neuve, Belgium). A wide variety of quadripolar or octapolar percutaneous electrodes for posterior funiculi stimulation are available from Medtronic, Inc. (Minneapolis, Minn.). As regards the neurostimulator (electrical device generating and delivering the electrical pulses), fully implantable systems (i.e., wherein the electrodes and neurostimulator, along with the power source, are implanted) can be used as can systems wherein only the leads and a radio-frequency receiver are implanted (the power source being worn externally with an antenna over the receiver). A detailed description of commercially available implantable surface electrodes and neurostimulators is provided at www.medtronic.com/neuro/paintherapies/pain_treatment_ladder/neurostimulation/stimulators_stim_sel/neuro_stim_stim_sel.html.

Certain aspects of the invention are be described in greater detail in the non-limiting Examples that follows. (See also U.S. Published Appln. 20030083716.)

EXAMPLE 1

It has been possible to disrupt aberrant synchronic activity of neural populations observed in normal mice partially depleted of dopamine or transgenic mice completely depleted of dopamine using stimulation of peripheral nerves, such as the trigeminal nerve. In these studies, a cuff electrode was chronically implanted around the infraorbital nerve, a branch of the trigeminal nerve. This approach was employed to test the efficacy of peripheral nerve stimulation, as compared to DBS, in alleviating motor impairment in: i) wild type mice in which dopamine was partially depleted, and ii) a transgenic animal model of PD (the DAT-KO mouse) in which dopamine was almost completed depleted from the brain. Preliminary results show that aberrant low frequency oscillations patterns of neural activity from the corticostriatal circuit induced by partial dopamine depletion in wild type mice can be decreased and locomotive activity restored by infraorbital stimulation (IS).

The first step of these studies consisted of determining the stimulation parameters (frequency and amplitude) optimum for reducing hypodopaminergic related aberrant synchronization in the corticostriatal circuit. This was achieved by systematic stimulation of the infraorbital nerve at different parameters along with recording of corticostriatal activity. Once the optimal values of frequency and amplitude were determined, an assessment was made of the effectiveness of these stimulation parameters in recovering gross locomotive activity and alleviating tremors and rigidity associated with dopamine depleted states. As control, the IS was compared to direct cortical stimulation, which is known to have effects similar to those to DBS. These experiments made it possible to compare the efficacy of the present procedure versus more conventional methods of brain stimulation.

Experimental Details

Parkinson's disease model. Dopamine transporter-knock-out (DAT-KO) mice lack the gene encoding the dopamine transporter, which is responsible for the re-uptake of extra-synaptic dopamine and replenishment of dopamine stores in the presynaptic terminal (Gainetdinov and Caron, Arum. Rev. Pharmacol. Toxicol. 43:261-284 (2003)). Treatment with the tyrosine hydroxylase inhibitor, α-methyl-p-tyrosine (AMPT), in these animals prevents dopamine synthesis which, along with the lack of the dopamine transporter, causes striatal dopamine concentrations to fall to 0.2% of the level observed in control animals (Sotnikova et al, PLoS Biol. 3:e271 (2005)). As a consequence, DAT-KO mice treated with AMPT display severe akinesia, rigidity, and tremors, resembling the terminal stages of PD in humans, for up to 16 hours (Sotnikova et al, PLoS Biol. 3:e271 (2005)). Therefore, dopamine depleted DAT-KO (DDD) mice provide an exceptional model for assessing the effectiveness of peripheral brain electrical stimulation as a potential therapeutic agent for PD.

Infraorbital nerve stimulation. In mice, IS is achieved by chronic bilaterial implantation of custom made platinum cuff-electrodes in the infraorbital nerve (Fanselow et al, J. Neurosci. 20:8160-8168 (2000)). Square biphasic pulses of 40 μs of duration, delivered at 1-130 Hz with amplitude of 0.011-0.5 mA, will be tested.

Peripheral nerve electrodes consist of two bands of platinum (0.5 mm wide and 0.025 mm thick, ~0.8 mm separation between bands) that run circumferentially around the nerve. The platinum bands are held in place and electrically insulated by a thin Sylgard coating. Each band is connected to a piece of flexible, 3-stranded Teflon-coated wire that is used to pass current between the two bands. The chronic implantation of these nerve cuffs requires general anesthesia in the rodents. After dissection of the trigeminal nerve, the cuff electrode is positioned around the nerve, such that the nerve stays surrounded by the cuff. The cuff is then tied around the nerve to hold it in place and the surgical wound sutured. The Teflon-coated leads from the platinum bands run subcutaneously where they were attached to a battery pack.

Neural activity recordings. In mice, a 32-electrode array is implanted targeting two structures affected in PD: dorsolateral (sensorimotor) striatum and primary motor cortex. Activity of single units (spikes) as well as activity of population or neurons (local field potential, LFP) will be acquired and recorded by an IMAP system.

Electromyogram (EMG). Muscular activity will be recorded from a wire attached to trapezium muscle.

Motor performance. The improvement of motor impairment upon IS is assessed by a variety of standard procedures described elsewhere as open field activity measurement, rotating rod test, akinesia test, catalepsy test, grasping test of muscular rigidity, bracing test and vertical pole test.

Results

Two C57/J (wild type) male mice where implanted with peripheral nerve cuff electrodes, microwire electrodes arrays in the striatum and motor cortex and one EMG wire in the trapezium muscle. After a week of recovery, a series of experiments were carried out. Individual animals were introduced to the open field activity (OFA) monitor cage, which permitted tracking of the animal's locomotive activity. After 10 minutes, the animal was injected with AMPT (250 mg/kg, i.p.) to produce a partial depletion in dopamine brain levels. The stimulation started 15 minutes after the injection. It was delivered in 2-minute windows, alternated with 2 minutes of rest (no stimulation). The amplitude was fixed at 0.4 mA. This value was selected on the basis that it produced a noticeable effect on the animal (soft scratching of the whiskers pads) at the onset of stimulation but no further signs of discomfort or pain. Sixteen different frequency values delivered in a pseudorandom way (1-130 Hz) were tested.

As seen in FIG. 5, dopamine depletion affected the activity of single units (see units dis1, dis2, m3, m4). Nevertheless, a dramatic effect on the population activity can be observed in the spectrogram. Before the AMPT injection, the oscillatory power of Local Field Potentials (LFPs) was broadly distributed between 0-8 Hz, while dopamine depletion produced a strong synchronization at 4 Hz, revealed as a clear red band that appears after time=600 s.

The key observation in these experiments was that IS at some frequencies could revert this strong neural oscillation pattern to the type of desynchronized firing activity observed during the control period. This effect allowed the animal to recover some locomotive activity as seen in the time period between 3600 and 4800. In order to quantify this observation, the ratio between the LFP power in the 2-4 Hz and 0-4 Hz range was used as an indicator of the predominant oscillatory pattern (FIG. 6). This measure was denominated dopamine spectral index. A dopamine spectral index close to 1 indicates a hypodopaminergic oscillatory pattern, while a spectral index close to 0.5 indicates a normal pattern.

As shown in FIG. 7, the dopamine spectral index clearly distinguished the oscillatory pattern observed during the control dopamine depleted (DD) conditions. In order to assess statistical significance, spectral index values were computed in 10-second windows, and grouped according the stimulation frequency or experimental condition (control or dopamine-depleted (DD)) for a multiple group comparison. In Animal 1, it was found that the spectral index during infraorbital stimulation at 40, 60, 80, 100, 120 and 130 Hz was significantly lower than in DD condition ($p<0.01$, ANOVA) and not different from basal condition. Of those, only stimulation at 120 HZ showed a significant recovery of locomotive activity ($p<0.01$, ANOVA). In Animal 2, stimulation at 1, 10, 30, 40, 70 and 120 Hz also showed significant differences with DD condition.

The preliminary results in wild type mice showed that the aberrant synchronized neural activity and the loss of motor activity, both related to partial hypodopaminergic condition (similar to early stages of PD), could be recovered by electrical infraorbital stimulation. These experiments will be repeated using a PD animal model, such as the dopamine-depleted DAT-KO mouse, to demonstrate that the stimulation of peripheral nerves is an effective treatment for almost complete dopamine depletion.

EXAMPLE 2

Experimental Details

Parkinson's disease model. C57BL/6 wild type male adult mice were used. Animals were treated with 250 mg/kg of the tyrosine hydroxylase inhibitor, α-methyl-p-tyrosine, every 2 hours, until akinesia and catalepsy were displayed. The key of this manipulation is a decrease of dopamine in the central nervous system to less than 40% of normal levels, thus resembling parkinsonian condition. Akinesia and was assessed by visual inspection, while catalepsy was assessed by a custom test. Treated animals exhibited those symptoms for several hours after last injection.

Posterior funiculi stimulation. (FIG. 4A) The electrode used to effect dorsal funiculi stimulation consists of two parallel platinum bands (each 2 mm in length, 0.3 mm in width and 0.025 mm thick) separated ~0.3 mm and embedded in surgical silicone (Sylgard). Each band is connected to a wire (Teflon-coated 7-strand stainless steel, 0.001 inches, bare diameter). (FIG. 4B) The electrode is implanted above the dorsal spinal cord and the connections wires are passed subcutaneously to an incision in the head skin and joined to a special connector attached to the skull. The connector is plugged to 2 stimulus-isolator units, which provide biphasic constant-current pulses at desired frequency and intensity. (FIG. 4C) Left: schematic dorsal view of the implanted electrode and the spinal cord. Right: schematic sagittal view of the implanted electrode. The electrode is inserted between vertebrae T1 and T2 and located longitudinally in close proximity to the dorsal surface of the spinal cord, over the posterior funiculi. Both ends of the electrode are trapped between the vertebrae and the spinal cord. r: rostral; c: cauda Stimulation experiment. Once in akinesic state, animals were subjected to a number of stimulation cycles. Each cycle comprised 5 stimulation paradigms of 30 second duration, regularly distributed in 1 hour. During the cycles, locomotive activity of the animal was measured by means of an array of infrared beams displayed in the bottom of the cage. Electrophysiological activity from primary motor cortex (M1) and dorsolateral striatum (STR) was recorded. These structures are related to initiation of volitional movement and their activity is severely altered in PD.

Results

Results are shown for two animals. Once in akinesic state, animals do not exhibit locomotive behavior. The delivery of strong air pulses to the body of the animal, which in a normal situation results in the mouse fleeing to another location in the cage, has no such effect in the akinesic animal (FIG. 8). However, stimulation of posterior funiculi at different frequencies will induce moderate to high levels of locomotive activity (FIG. 8). Stimulation at 300 Hz appears to be effective in all treated animals (data not shown). The observed behavior exhibited during stimulation by different animals is consistent. Once stimulation starts, the animal will stretch all four limbs in a rapid single movement. After a few seconds, the mouse will start moving around the field.

In order to identify a possible mechanism for akinesia relieved by PFS, the activity of M1 and STR neurons was analyzed. M1 and STR neurons change their firing rates (increase or decrease) when the animal is engaged in motor activity (Costa et al, Neuron 52:359-369 (2006)). Such a trend was observed during PFS stimulation, with neurons increasing or decreasing firing rate. An example is shown in FIG. 9A. A summary for the results in Animal 1 is shown in FIG. 9B. PFS at 300 Hz, the most successful paradigm for inducing locomotion, is also the one that produced significant changes in firing rate in most neurons, namely 9 out of 10 M1 neurons and 3 out of 9 STR neurons. On the other hand, 10 Hz PFS, which is not effective in inducing locomotion in this animal, produce firing rate changes only in 2 out of 10 M1 neurons and 3 out of 9 STR neurons.

Local field potential (LFP), which is a measure of synchronized neural population activity, was also recorded from M1 and STR during PFS delivery. Dopamine depletion related akinesia, such in PD, is related to strong synchronization at low frequencies (<10 Hz), which is observed as an increase in LFP oscillatory activity at low frequencies and a decrease in oscillatory power at high frequencies (>30 Hz). PFS at 100 Hz and 300 Hz reverse this trend in both M1 and STR, increasing oscillatory power in the range 30-90 Hz and decreasing it at low frequencies (FIG. 10). This effect prevails even after stimulation period is over (FIG. 10).

In summary, the results indicate that high frequency PFS (100 Hz and 300 Hz) is effective in disrupting aberrant low frequency synchronization in motor related neural circuits, thus facilitating the initiation and execution of volitional movement.

EXAMPLE 3

Experimental Details
Animals

In total 28 wild-type and 8 DAT-KO C57/BL6J mice and 8 Long-Evans rats were used. Animals were kept on a 24 hour day-night cycle and received food and water ad libitum. All the procedures involving animals were done according the protocols approved at Duke University.

Surgery

In a single surgery both stimulation and recording electrodes were implanted under deep Ketamine/Xylozine anaesthesia (50-90 mg/kg). The flat stimulation electrode was inserted between vertebrae T1 and T2 in mice and between T2 and T3 in rats placed longitudinally in the epidural space over the dorsal columns, thereby being in close proximity to the dorsal surface of the spinal cord. Both ends of the electrode were inserted under the laminae of the vertebral arcs of the adjacent vertebrae effectively stabilizing the implant. For trigeminal stimulation, cuff-electrodes were implanted bilaterally in the infraorbital nerve as previously described (Fanselow et al, J. Neurosci. 20:8160 (2000)).

Tissue Dopamine Content Analysis

Striatal tissue content of dopamine was assessed using high performance liquid chromatography with electrochemical detection, as previously described. Striata were rapidly dissected, frozen, and stored at −80° C. Later, tissue samples were homogenized in 0.1M HClO4 containing 100 ng/ml 3,4-dihydroxybenzylamine (DHBA) as an internal standard. Homogenates were centrifuged for 10 min at 10,000×g. Supernatants were filtered through 0.22 µm filter and analyzed for levels of dopamine using HPLC-EC. Monoamines and metabolites were separated on a microbore reverse-phase column (C-18, 5 µm, 1×150 mm, Unijet, BAS). The volume of injection was 5 µl.

Striatal 6-OHDA Lesions

Rats received a total of 21 µg 6-OHDA, injected in 3 locations of the striatum on each side. The injections contained a saline solution with 3.5 mg/ml 6-OHDA and 0.05% ascorbate. Anteroposterior, mediolateral and dorsoventral coordinates for the injections were: +1.0, +/−3.0, −5.0; −0.1, +/−3.7, −5.0 and −1.2, +/−4.5 and −5.0 (Winkler et al, Neurobiol. Dis. 10:165 (2002)).

Tyrosine-Hydroxylase (TH) Staining and Quantification

The extent and position of striatal lesions was confirmed by TH immunohistochemistry. For quantification of TH-staining, digital photos of the individual sections were taken with a 16× microscope (Stemi 2000-c, Zeiss) under identical illumination conditions. The range in brightness was practically identical for every photo ranging from no light (inside the microscope) at the outer edge to the brightest non-stained part of each section. Images were converted to grey-scale bitmap format with an 8-bit dynamic range in brightness. Pixels with an intensity ranging from ⅕ to ⅔ of maximum were found to include all stained parts of the sections, as confirmed by visual inspection. The staining and number of pixels with a brightness corresponding to this interval was quantified for all sections taken from the same part of the brain in a sham treated and lesioned rat, respectively (FIG. 21) and the 6-OHDA lesioned animal was found to have only 21% of the sham treated animal.

Stimulation Electrodes

The flat electrodes used for dorsal column stimulation consisted of 2 platinum bands, for mice: 2 by 0.3 mm and rats: 4 by 0.9 mm (platinum foil thickness 25 µm; Goodfellow Cambridge Ltd, Huntingdon, England) positioned parallel to each other. Each band was connected to a thin stainless steel wire (teflon-coated 7-strand, 25 µm, bare diameter) with silver paint at the upper surface. The assembled components were embedded in surgical silicon, leaving the lower surface exposed. For trigeminal nerve stimulation cuff-electrodes surrounding the infraorbital nerve branch were manufactured according to previously described techniques, except size was reduced to fit the mice (Fanselow et al, J. Neurosci. 20:8160 (2000)).

Recording Electrodes

S-isonel-coated tungsten wire electrodes (33 µm, California Fine Wire, CA) were assembled into 2×8 arrays and cut into two groups with two different lengths matching the distances to the dorsolateral striatum and the infra-granular layer of the primary motor cortex (Costa et al, Neuron. 52:359 (2006)). For EMG recordings, a single-ended stablohm microwire electrode (50 µm) was inserted in the nuchal muscles. The microwires were attached to a printed circuit board with a miniature connector (Omnetics Connector Corp., MN) attached to the opposite side of the circuit board.

Open-Field Experiments

Rats were placed in a circular open-field (90 cm diameter) for 70 min (10 min adaptation and 1 h behavioural recording). The animals were then allowed to rest in its home cage for one hour. After that, the animals were reintroduced into the open-field and dorsal column stimulation (DCS) was applied every 10 minutes for 30 seconds. In mice, locomotion was documented both by video recordings and through an automated tracking system based in infra-red beams (Med Associates Inc., VT). Recordings were obtained before and after dopamine-depletion, and DCS was applied as described below.

The movements of the rats in the open-field were extracted from the digitized video recordings, with approximately 1 mm spatial resolution, with custom designed algorithms implemented in command interpreting software (The MathWorks Inc., MA). For mice, scored locomotion from the infra-red tracking system was binned into 500 ms bins (original resolution 50 ms). For locomotion extraction from video data, single frames with a 500 ms interval were used. Locomotion data collected by both techniques were fully comparable as confirmed by multiple calibration sessions.

Electrical Stimulation

DCS and infraorbital nerve stimulation consisted of biphasic square constant current pulses of 1 ms duration each phase, delivered at 10, 100 and 300 Hz (Master-8 Stimulator, A.M.P.I., Israel).

Signal Acquisition

LFPs, EMGs and single- and multi-unit activity were recorded using a multichannel recording system (Plexon Inc, TX). LFPs and EMG were pre-amplified (500×), filtered (0.7-170 Hz), and digitized at 1000 Hz using a digital acquisition card (National Instruments, Austin, Tex.). Action potentials were split-off in the pre-amplifier by a band-pass filter (154 Hz-8.8 kHz) and digitized at 40 kHz.

Data Analysis

LFPs were corrected off-line for frequency dependent phase-shifts induced by the hardware filters (Nelson et al, J. Neurosci. Methods 169:141 (2008)). To avoid high-amplitude movement artefacts we discarded data from <1.5 Hz oscillations. Response latencies of LFP changes in MI and striatum following DCS onset was estimated from single pulse evoked potentials (1.3 T at 0.5 Hz)

Single- and multi-units were sorted according to their wave forms using the off-line sorter software from Plexon (Plexon, Inc., Texas). The criteria used for single unit classification was that spike shapes were clearly different from other spikes as judged by a cluster separation in feature space (Lin et al, J. Neurophysiol. 96:3209 (2006)) and the absence of spiking activity during the refractory period (less than 0.1% of spikes occurring within 2 ms of another spike). Units not fulfilling the latter criterion were classified as multi-units.

To determine whether a neuron changed its firing rate after a particular treatment, a firing-rate distribution of the period preceding the treatment (0.5 s bin for pre-locomotion analysis, 1 s bins for post-DCS analysis) was generated and the 99% confidence interval calculated based on a Poisson distribution. A neuron was considered to have changed firing rate if the firing frequency of at least one (pre-locomotion and post-DCS analysis) or 60% (non-depleted/depleted analysis) of the post-treatment bins were beyond the confidence interval limits. The firing rates depicted in the figures were smoothed with a moving average window of 2 seconds. Spectrograms of LFPs were based on a 4 s window (1 s sliding step) using multitaper method with five tapers (Percival et al, Spectral analysis for physical applications: multitaper and conventional univariate techniques (Cambridge University Press, Cambridge; New York, N.Y., USA, pp. xxvii, p. 583 (1993)), unless otherwise stated.

For detecting changes in spectral index around spontaneous locomotion, the spectral index was calculated from a LFP spectrogram of 1.024 s window sliding every 0.05 s in the periods around locomotion onset [−12 s, 12 s] and in non-locomotion periods [−22 s, −12 s]. Locomotion period spectral index values above a 99% confidence interval, based on a Poisson distribution from the no-locomotion spectral index values, were considered significantly different.

Spike-LFP Entrainment Analysis

Units were classified as entrained to LFP when they displayed maximum STA amplitude greater then 99.9% of 1000 simulated STAs with original LFP segment and pseudo-random spike time stamps preserving the average firing rate. Preferred power of the STA was determined as frequencies showing power greater then 99% of the spectra of the simulated STA LFP. All STA LFPs were calculated in a [−256 ms +256 ms] window.

Statistics and Numerical Operations

For statistical tests, whenever distributions did not pass normality tests (D'Agostino and Pearson omnibus normality test), non-parametric versions such as Mann-Whitney (t-test) or Kruskal-Wallis (ANOVA) were used. In the latter case, Dunn's multiple comparison test was used as a post test if significant (p<0.05) differences were detected in the initial test.

The variance for ratios were calculated as:

$$\mathrm{Var}(X/Y) = E[Y^2]\mathrm{Var}(1/X) + \mathrm{Var}(Y)E[1/X]^2$$

assuming $E[X]=\mathrm{mean}(X)$ and $E[Y]=\mathrm{mean}(Y)$. After that, Z-scores were calculated for relevant comparisons of pairs of ratios as $(\mathrm{mean}(X)-\mathrm{mean}(Y))/\mathrm{sqrt}(\mathrm{Var}(X)-\mathrm{Var}(Y))$ and Bonferroni corrected for multiple comparisons.

The number of bins used for histograms of locomotion speeds was adjusted according to the maximum speed scored in a single bin in the slowest condition (i.e. 500 mm/s for the rats and 180 mm/s for the mice). The relatively few (<0.3%) events with locomotion components faster than the upper limit found in the other conditions were assigned to the fastest bin. The number of events within each speed interval was summed and the relative change in response to DCS was calculated. A lower threshold just above the quantal step was used in the analysis of histogram distributions, i.e. 10 mm/500 ms for both mouse and rat data.

Results

The potential of electrical stimulation of the dorsal column afferent pathways in the spinal cord was evaluated, as a strategy for treating motor symptoms in two animal models of PD. Experiments were aimed at establishing both electrophysiological and behavioral effects of dorsal column stimulation (DCS). This was achieved by chronically recording the neuronal activity from the dorsolateral striatum and primary motor cortex in animals placed in an open-field experimental set-up. During these experiments, an investigation was made as to whether DCS, like DBS, would allow for a reduction of L-DOPA doses used for treatment of motor symptoms.

Dopamine, Akinesia and Synchrony

Figure 11:
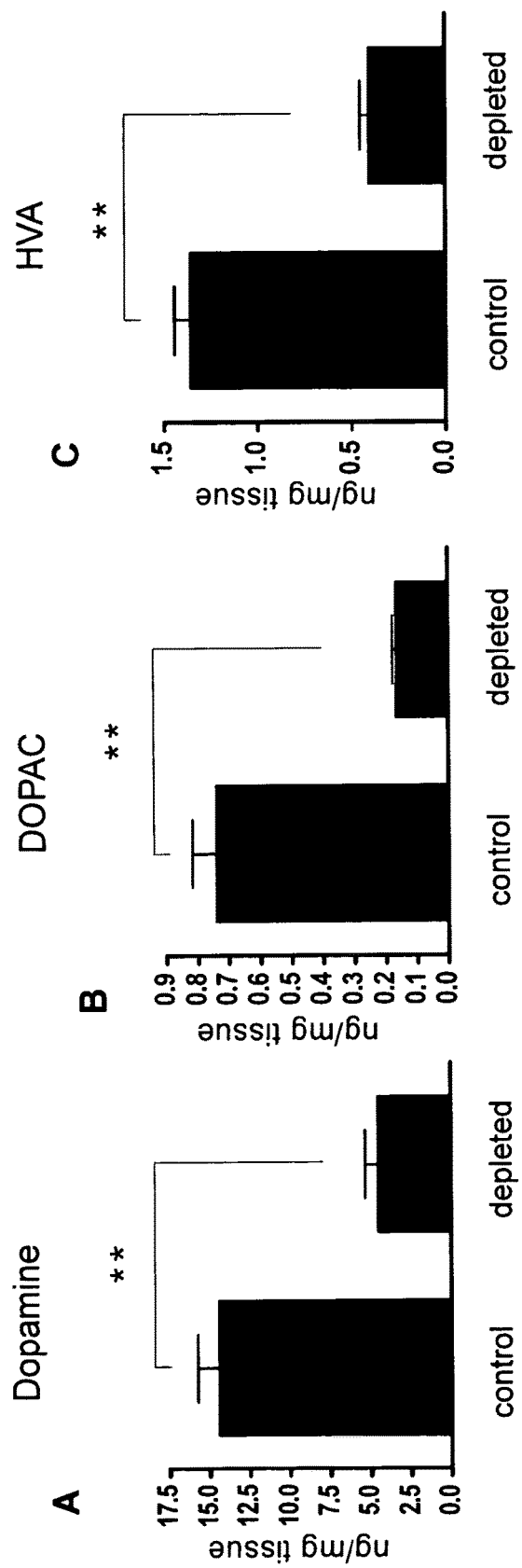
FIGS. 11A-11C. Tissue content analysis confirms that acute pharmacological dopamine depletion in wild-type mice leads to striatal dopamine levels similar to those observed in PD patients. Two i.p. injections (250 mg/kg), administered 2 hours apart, of the tyrosine hydroxylase inhibitor alpha-methyl-para-tyrosine (AMPT) in wild-type C57/BL6J mice, reliably decreased striatal levels of dopamine (FIG. 11A) and its metabolites 3,4-Dihydroxy-Phenylacetic Acid (DOPAC) (FIG. 11B) and Homovanillic acid (HVA) (FIG. 11C), as measured 4 hours after the last AMPT injection (see FIG. 14). Average quantities in depleted animals were reduced for dopamine, DOPAC and HVA to: 4.5 ng, 0.17 ng and 0.41 ng per mg tissue, respectively, compared to 14.4 ng, 0.74 ng and 1.36 ng per mg tissue, for saline injected control animals (**=$p<0.005$, Mann-Whitney test, n=6 in each group). Tissue content analysis of dopamine and metabolites.
Figure 12:
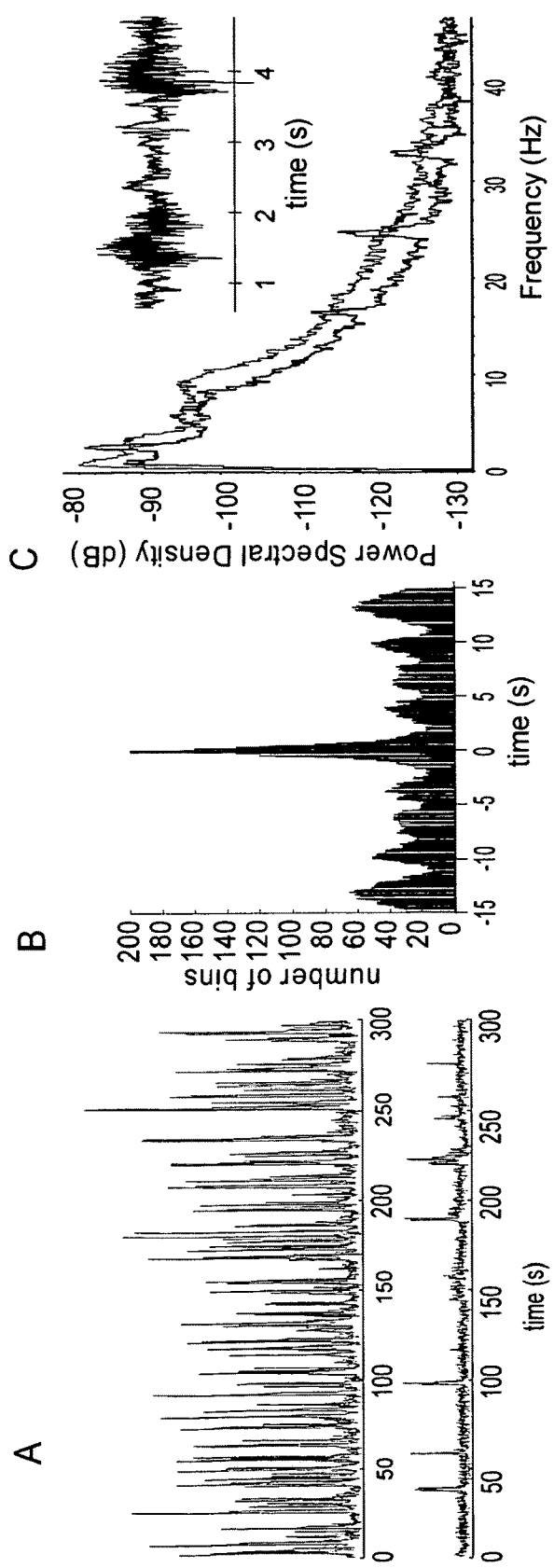
FIGS. 12A-12C. Acute pharmacological dopamine depletion causes parkinsonian like tremor.
Figure 13:
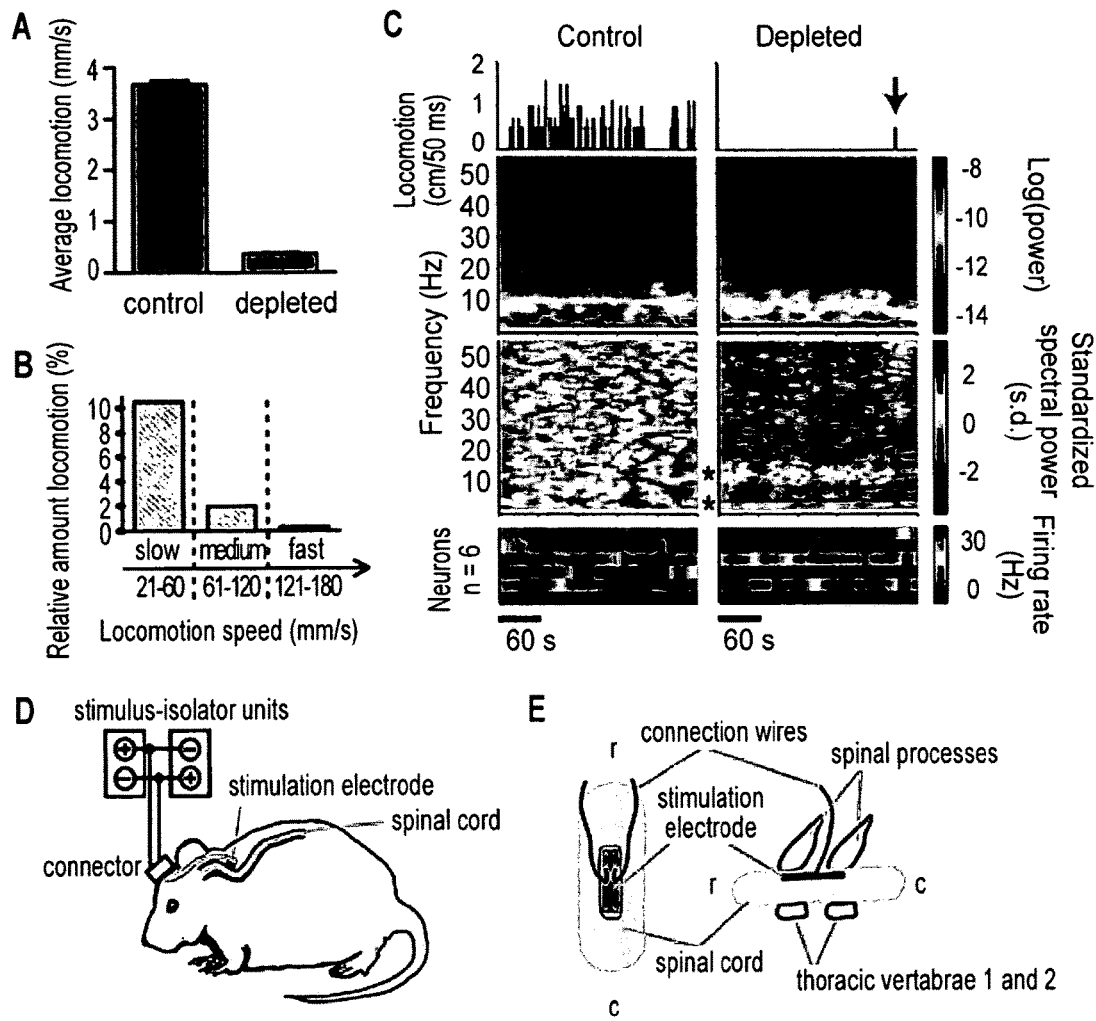
FIGS. 13A-13E. Acute inhibition of dopamine synthesis produces a parkinsonian state.

The first set of experiments was carried out using an inducible mouse model of PD, first in wild-type animals and then in dopamine-transporter knock-out (DAT-KO) mice (Sotnikova et al, PLoS Biol. 3:e271 (2005)). Through pharmacological inhibition of dopamine synthesis, acute dopamine depletion was induced in both types of animals in order to reliably document the effects of DCS during a severe parkinsonian-like state of akinesia. In agreement with previous experiments, the characteristic behavioral and electrophysiological changes following inhibition of dopamine synthesis was confirmed in these animals (Carlsson, Acta Neurol. Scand. Suppl 51:11 (1972), Costa et al, Neuron. 52:359 (2006), Sotnikova et al, PLoS Biol. 3:e271 (2005)). In patients, the cardinal symptoms of idiopathic PD, rigidity, resting tremor and brady-/hypokinesia, have been reported to be clinically apparent following degeneration of 60-70% of the dopaminergic neurons of the substantia nigra pars compacta, which in turn results in a 30-50% reduction of striatal dopamine levels (Brooks et al, Biol. Psychiatry 59:908 (2006), Lloyd et al, J. Pharmacol. Exp. Ther. 195:453 (1975)). In these experiments, acute pharmacological dopamine depletion in wild-type C57/BL6J mice was achieved with two i.p. injections (250 mg/kg) of the tyrosine hydroxylase inhibitor alpha-methyl-para-tyrosine (AMPT) during a 6 h period. This treatment produced a 69% reduction of striatal dopamine levels, as confirmed by dopamine tissue content analysis (mean±SD=4.5±2.0 ng dopamine per mg tissue in depleted animals compared to 14.4±3.3 in controls; p<0.005 Mann-Whitney, n=6/6 (FIG. 11), slightly below the levels observed in PD patients (Brooks et al, Biol. Psychiatry 59:908 (2006), Lloyd et al, J. Pharmacol. Exp. Ther. 195:453 (1975)). Equivalent symptoms to all the main clinical motor manifestations in PD patients were found in AMPT-injected mice after the 6 h depletion period. Firstly, rigidity was displayed in the form of severe catalepsy assessed as the inability to remove the forepaws for at least 30 s from a bar placed 3 cm above the ground (under normal conditions animals remove the forepaws immediately (Sotnikova et al, PLoS Biol. 3:e271 (2005)). Secondly, a pronounced muscle tremor was evident during resting periods, which was reflected in characteristic oscillatory patterns in electromyographic (EMG) recordings obtained from chronically implanted microwires in the nuchal muscles (FIG. 12). This tremor was suppressed during locomotion bouts. Thirdly, and perhaps the most evident behavioral change associated with the dopamine-depleted condition, there was a substantial decrease in the amount of locomotion displayed in the open-field. Dopamine-depleted animals showed a decrease in the average amount of locomotion during testing periods that corresponded to ~10% of control values [average locomotion scores in non-depleted and depleted animals were (mean±SEM) 3.7±0.1 and 0.4±0.02 mm/s, n=11 and 14, respectively] (FIG. 13A, see also Drouot et al, Neuron 44:769 (2004) and Sakai et al, Brain Res. 633:144 (1994)). Further, a detailed analysis of locomotion episodes in terms of movement speed showed that the reduction was most prominent for high- and medium-speed components reflecting a noticeable bradykinesia in the depleted state (locomotion scores in depleted animals expressed as percentage of the scores in non-depleted animals were, slow: 10.5%, medium: 2.0%, fast: 0.3%; FIG. 13B).

In parallel with the overt changes in locomotive ability after dopamine depletion, neuronal activity patterns of dorsolateral striatum and primary motor cortex (MI) were also significantly altered. Differences were found both on a population level, through inspection of local field potentials (LFPs), and in the firing patterns of single cortical and striatal neurons. These were in agreement with previous studies indicating prominent and rapid changes in corticostriatal neuronal ensemble coordination after acute dopamine depletion (Costa et al, Neuron. 52:359 (2006)). To begin with, local field potentials (LFPs) were analyzed; these voltage fluctuations are considered to reflect alterations in the synaptic drive of neurons in the recorded area and, to some extent, the postsynaptic activation of populations of neurons surrounding the recording site (Mitzdorf, Physiol. Rev. 65:37 (1985), Berke et al, Neuron. 43:883 (2004)). An example of LFP spectrograms recorded in MI during two 5-min periods before and after dopamine depletion is shown in FIG. 13C (second and third rows, left and right, respectively). The spectral shift to lower frequencies in the depleted state is evident. Spectral analysis revealed particularly powerful oscillations around 1.5-4 Hz and in the lower beta range (10-15 Hz), whereas the power of oscillations >25 Hz was decreased in relation to baseline conditions (standardized spectrograms, FIG. 13C, third row and FIG. 14). Note, however, that the spectral power was somewhat normalized during the brief locomotion episode at the end of the 5-minute recording period.

Figure 14:
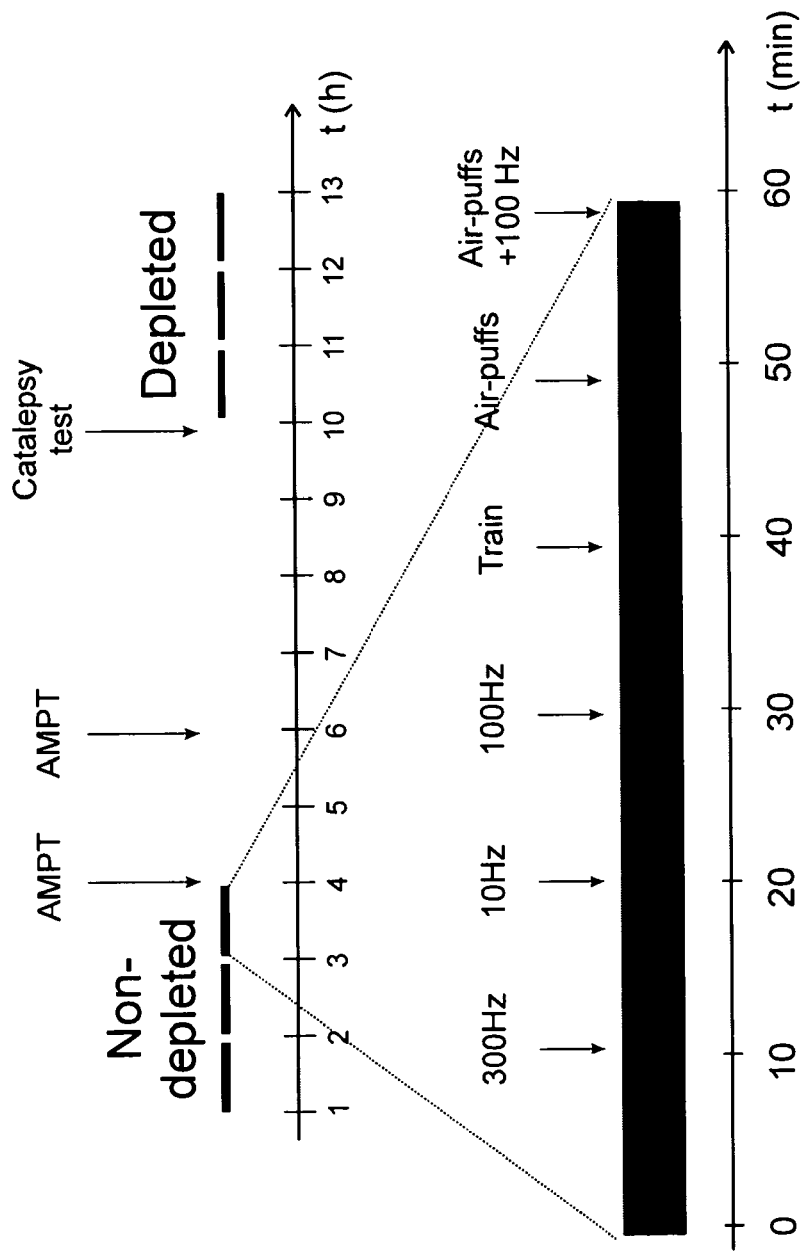
FIG. 14. Summary of experimental protocol for DCS evaluation in acutely dopamine-depleted wild-type mice. Each animal was stimulated using six different types of stimuli (applied every tenth minute) in three identical cycles during both control conditions (green bars) and in the depleted state (red bars). After baseline data had been acquired, the animals received two AMPT (250 mg/kg)

In general, high-frequency oscillations were more prominent in the non-depleted relative to the depleted condition. Still, low-frequency oscillations could be found in non-depleted animals during resting periods, although these oscillations were typically not in the same frequency range as those found during dopamine depletion, but rather at higher band around 4-9 Hz. When analysing single- and multi-unit activity in the normal and dopamine-depleted states, important differences were also found. The firing rates of a majority of 52 striatal and cortical neurons, which were positively identified after 6 hour depletion period, showed significant differences (70.0% in motor cortex and 75.0% in striatum, $\alpha$=0.001) when the more active non-depleted state and the immobile depleted condition were compared (as exemplified by the activity raster plots shown for a few units in FIG. 13C, bottom row). It was also observed that during dopamine depletion, a higher proportion of neurons tended to discharge phase-locked to LFP oscillation, in effect resulting in increased synchronicity (overall, 52.7% [64/129] of the recorded units showed entrainment of action potentials to the LFP oscillations after dopamine depletion as compared to 37.0% [44/127] in the non-depleted condition; $\alpha$=0.001; FIG. 14).

Taken together, the robust behavioral changes and the characteristic differences found between the depleted and non-depleted states with regard to both LFP oscillations and firing patterns of populations of single neurons confirmed that acute dopamine depletion provided a reliable experimental model for comprehensively characterizing the effects of DCS specific to the Parkinsonian state.

DCS Alleviates Akinesia and Synchrony

The effect of DCS was next evaluated in mice before and after acute pharmacological dopamine depletion. DCS was achieved by chronic implantation of custom-made flat bipolar platinum electrodes positioned epidurally above the dorsal columns of the spinal cord at the upper thoracic level (FIGS. 13E and 13F). Animals were stimulated for 30 s every tenth minute. Four DCS paradigms were used: continuous stimulation at 10, 100 or 300 Hz, or stimulation in trains of 8 pulses at 100 Hz every two seconds. In addition to electrical stimulation, air-puffs (0.25 Hz targeted directly to the animal) either alone or in combination with 100 Hz continuous DCS were also tested, completing a 1-h cycle of six stimulation paradigms. The same stimulation cycle was repeated three times, both before and after dopamine depletion (FIG. 15). Finally, in a separate set of experiments, the effect of bilateral trigeminal nerve (infraorbital branch) stimulation was investigated using the same experimental paradigm (rightmost bars in FIG. 16A). Stimulation intensities were individually adjusted according to the response thresholds of each animal and each stimulus type. Typically, a startle response or a sudden change in whisking behaviour was taken to indicate threshold level (T) for response to stimulation. For DCS ~1.3 T was used in all experiments (mean±SD at 300 Hz=333±138 µA), while for trigeminal nerve stimulation ~1.1 T was used (mean±SD at 300 Hz=54±20 µA) in order to avoid activating nociceptive afferent fibres present in this nerve.

Figure 17:
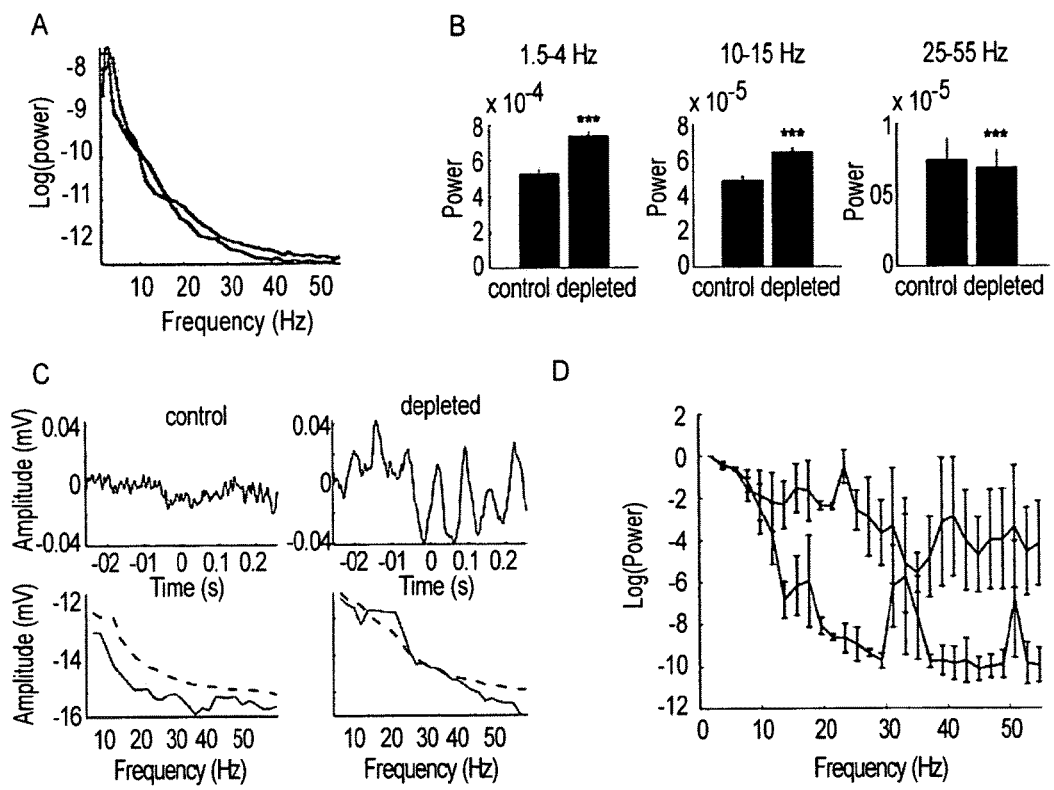

After three stimulation cycles under control (non-depleted) conditions, animals were injected with AMPT and acquisition of data related to the dopamine-depleted state commenced when animals displayed clear catalepsy (according to the test criterion described above). It was found that DCS had a dramatic effect on the amount of locomotion displayed during stimulation periods in the dopamine-depleted animals. This effect was strongest for 300 Hz stimulation; on average the amount of locomotion during stimulation periods was more than 26 times higher than during the 5 minute period prior to stimulation (FIG. 16A). DCS had a smaller, albeit clear effect, using lower stimulation frequencies (FIG. 16A and FIG. 17). In contrast, air-puffs alone or trigeminal nerve stimulation were not effective, suggesting that the locomotive recovery observed is specific to the stimulation of dorsal column pathways and is not a mere consequence of arousal or pain. DCS caused increased locomotion also during non-depleted conditions, but this increase was moderate (4.9 times pre-stimulus values at 300 Hz) in comparison to that in depleted animals (26 times; FIG. 16A). Locomotion was normally initiated a few seconds after the onset of DCS, with a slightly longer delay in depleted animals (median=3.35/1.35 s, interquartile range=2.22/1.22 s, p=0.023, Mann-Whitey, in depleted/non-depleted animals, for 300 Hz stimulation). However, a small residual effect was also found after high-frequency stimulation in depleted, but not in non-depleted animals (3.4 and 0.95 times pre-stimulus values, respectively for 300 Hz DCS during the 30 s following stimulation). In addition to the strong improvement in general locomotive capability, DCS also proved efficient for alleviation of bradykinesia as indicated by the relatively larger increase in the amount of fast movement components in depleted animals (FIG. 16B).

Struck by the dramatic functional recovery on the behavioral level, the electrophysiological changes associated with motor improvements were analyzed next. Analysis of LFP recordings during DCS in both MI and in striatum showed a strong shift in spectral power from lower frequencies to higher (average spectrograms from a total of 21 events of DCS at 300 Hz obtained from 9 animals are shown in FIG. 16C). The spectral shift was maintained throughout the stimulation period and lasted for ~50 s following the off-set of stimulation. This indicates a prolonged shift in the activity state of these brain structures, also ruling out any major effects of contamination in the spectrograms from stimulation currents (FIG. 16C). To condense the spectral shift into a single measure, a spectral index was computed by dividing the spectral range analyzed into an upper and lower half and calculating the ratio of the summed power of the frequencies in the two intervals [(25-55 Hz)/(1.5-25 Hz)]. The spectral index (black trace in FIG. 16C) clearly illustrates the rapid spectral shift induced by DCS and the prolonged effect after DCS had ceased.

DCS also affected the firing patterns of individual neurons. To avoid interference from stimulation artefacts, the 30 second stimulation periods were excluded from the analysis of spike data. But even during the period following stimulation, numerous neurons showed significantly altered firing rates (47.9% in MI and 41.8% in striatum, $\alpha=0.01$; FIG. 16C, row 4 and 5, respectively). The fraction of units entrained to LFP dropped notably (from 42.7/38.8% in MI/striatum the 30 s before DCS to 24.5/24.0% the 30 s after DCS, $\alpha=0.01$). Thus, DCS was shown to have a prominent effect on activity patterns in both MI and in striatum and to reduce the aberrant synchronization representative of the dopamine depleted state.

Although the onset of locomotion was delayed a few seconds, changes in the neural activity were detected almost immediately following DCS onset (mean±SD evoked potential latency=44±5 ms), perhaps indicating that the electrophysiological changes have a permissive rather than directly instructive role for the initiation of locomotion. It is consequently an intriguing possibility that the impressive behavioral improvements obtained with DCS are mediated by desynchronization of the activity of corticostriatal circuits, an event that may create a state permissive of movement initiation, even in Parkinsonian animals, where initiation of movement is otherwise impaired.

A Brain State Permissive of Locomotion

In the initial characterization of the dopamine-depleted state above it was noted that during the relatively rare instances when the depleted animals displayed locomotion, low-frequency oscillations were diminished (FIG. 16C). This situation bears an obvious resemblance to the DCS induced state. Thus, a certain decrease of low-frequency oscillations may be required to initiate locomotion. To get a better understanding of the changes in the activity of MI and striatum neurons associated with the initiation of locomotion, the detailed temporal patterns of shifts in oscillatory LFP activity were analyzed during spontaneous locomotion events in non-depleted (115 events in 10 animals) and depleted mice (51 events in 5 animals) (FIGS. 18A and 18B). In both states, significant spectral shifts (p<0.01, see Experimental Details) from lower to higher frequencies were detected a number of seconds prior to the initiation of locomotion (non-depleted: mean±SD=2.9±1.7 s, range 0.1-5.5 s, n=88, MI and striatal LFPs; depleted: 3.0±1.7, range 0.2-5.5 s, n=48, MI and striatal LFPs). Yet, there were also important differences, most notably below 25 Hz. A more differentiated decrease in power of oscillations below 8 Hz and an increase above 17 Hz was observed in non-depleted animals, whereas the spectral power in a broader range between 5 and 25 Hz was decreased in depleted animals. Since these different patterns occurred before the onset of locomotion, it is unlikely that they were due to differences in locomotion between the two groups. Instead, they could be part of the explanation why depleted animals moved slower and for shorter time periods. In addition to LFP activity patterns, striking parallels between spontaneous locomotion and DCS-induced brain changes also existed on the level of single neurons. In fact, the same type of firing rate changes that were found following DCS also occurred in conjunction with spontaneous locomotion events. From a total pool of 193 neurons (from 9 control and 5 dopamine-depleted recordings sessions in 11 animals), 111 modulated their firing rate during locomotion and unexpectedly, 59 of these neurons showed a pattern of early activation, 2.9±1.4 s (mean±SD) before actual locomotion onset (range=0.5-4.5 s, n=59 striatal and MI units from depleted and non-depleted conditions, FIG. 18C).

Altogether, the close electrophysiological parallels between DCS and spontaneous locomotion suggest that DCS brings the activity of corticostriatal circuits in dopamine-depleted animals back to a brain state that normally precedes locomotion. Accordingly, DCS could in this way facilitate initiation of locomotion in the Parkinsonian state.

DCS in Combination with L-DOPA Treatment

In spite of improved techniques for DBS, pharmacological treatment still remains the preferred choice for most PD patients. However, an important feature of DBS is that it permits a reduction of L-DOPA dosage, thereby minimizing the long-term side effects associated with pharmacotherapy (Perlmutter et al, Annu. Rev. Neurosci. 29:229 (2006)) and extending the beneficial time period of pharmaceutical treatment. Because the implantation of an epidural stimulation electrode over the dorsal columns constitutes a substantially less invasive surgical procedure than the implantation of DBS electrodes, a combined effect of DCS with lower doses of L-DOPA could potentially allow more patients to benefit early on from this combined therapy, while improving their quality of life. Therefore, the extent to which DCS could substitute for, or reduce, the L-DOPA doses needed to allow for locomotion was evaluated.

In order to find the minimum dose of L-DOPA (alone or combined with DCS) required to restore locomotion, a severely dopamine-depleted akinetic animal model was used, namely mice lacking the gene for the presynaptic dopamine membrane transporter (DAT-KO). Since the transporter normally recycles a large portion of the released dopamine, these mice display >95% decrease in the striatal content of dopamine (Sotnikova et al, PLoS Biol. 3:e271 (2005)). These levels of dopamine can be further decreased to virtually undetectable levels by a pharmacogenetic approach, injecting AMPT (250 mg/kg i.p.) to inhibit the synthesis of dopamine, resulting in a completely akinetic animal model (Sotnikova et al, PLoS Biol. 3:e271 (2005)). Thus, by gradually increasing dopamine levels through repeated L-DOPA injections every hour, it was possible to probe the locomotion thresholds. DCS (1.3 T at 300 Hz) was applied every fifth minute, from 15 to 35 minutes post-injection in the L-DOPA+DCS group (it was during this time period that animals were observed to start moving in the L-DOPA only group). In the group receiving only L-DOPA injections (n=6 sessions from 4 mice), locomotion typically first occurred after the fifth injection (5 mg/kg dose, corresponding to a total dose of 15 mg during the first five hours). When L-DOPA treatment was combined with DCS, the same amount of locomotion was displayed after the second injection (2 mg/kg dose, corresponding to a total dose of 3 mg in the first two hours) (n=10 experiments from 7 mice, FIG. 19A). That means that ⅕ of the L-DOPA total dose, when used in combination with DCS, was enough to produce equivalent locomotion effects achieved when L-DOPA alone was chosen as a treatment. In fact, overall, there was also a general increase in the amount of locomotion displayed in the L-DOPA+DCS group over the entire range studied. Thus, L-DOPA+DCS seems to be superior to L-DOPA alone in terms of the ability to rescue locomotive capability after severe dopamine depletion. Finally, it was noted that animals in the L-DOPA+DCS group consistently showed higher values of spectral index than the L-DOPA only group. This suggests that DCS facilitates locomotion, even in severely depleted animals, through similar mechanisms (FIG. 20).

DCS is Effective After Chronic Lesions

Although the acute dopamine depletion model employed in the first set of experiments was shown to reproduce all the main symptoms of PD, it was important to confirm the effectiveness of DCS in an animal model that also involves loss of nigrostriatal dopaminergic connections. In these experiments, chronic dopaminergic denervation of the striatum was achieved using 6-OHDA lesions in rats (n=4). After bilateral 6-OHDA lesions (three sites per side), rats displayed progressive deterioration of motor function and sustained weight loss, both cardinal signs of successful lesioning in this widely used animal model (Cenci et al, Nat. Rev. Neurosci. 3:574 (2002), Winkler et al, Neurobiol. Dis. 10:165 (2002)). One month after lesioning, several motor impairments were apparent, including abnormal posture and gait, hypokinesia, bradykinesia, and reduced forelimb dexterity (for example manipulating food pellets). When placed in the open-field, 6-OHDA lesioned rats displayed reduced locomotion compared to another group of rats (n=4), which received vehicle injections in identical sites in the striatum (mean±SEM=2.85±0.068 and 7.78±0.144 min/s on average, respectively). Quantification of immunohistochemical staining of the dopamine synthesizing enzyme tyrosine hydroxylase in brain sections of sham-lesioned and 6-OHDA treated rats indicated that lesioned rats had only ~20% of the immune-signal found in sham-lesioned animals (FIG. 21), confirming a specific effect of 6-OHDA on the loss of dopaminergic neurons.

Lesioned rats were then tested during two one-hour sessions in the open-field, the first hour without stimulation and the second with DCS applied for 30 s every tenth minute (1.3 T, 300 Hz, mean±SD intensity for sham and lesioned: 286.6±119.9 μA and 233.4±53.7 μA, respectively). In the lesioned group, DCS resulted in remarkably increased amounts of locomotion compared to the first hour, whereas sham animals actually moved less during DCS sessions than during the non-DCS sessions (FIG. 19C). Hence, in agreement with the findings in the wild-type dopamine-depleted mouse model (FIG. 16A), there were also specific improvements of motor function in the Parkinsonian state compared to controls in a chronic lesion model of PD. In lesioned rats, DCS not only alleviated hypokinesia during stimulation, but it also caused an increase in locomotion after the stimulation period. This residual effect lasted around 100 s. (FIG. 19B). Comparing the average distance travelled per second in DCS and non-DCS sessions for lesioned and sham animals, respectively, yielded significant differences between all four conditions (p<0.001, Kruskal-Wallis and Dunn's multiple comparison test, FIG. 19C).

The effect of DCS on bradykinesia in 6-OHDA lesioned rats was also evaluated. The relative change in the number of locomotion events scored in each movement speed interval (slow, medium and fast) for DCS compared to non-DCS sessions was calculated for sham treated and lesioned animals. Lesioned animals showed a relative increase in the number of scored locomotion events for all movement speeds. This effect was more pronounced for faster movements, indicating a specific effect on bradykinetic symptoms in addition to the general improvement in the overall amount of locomotion (FIG. 19D). In summary, a similar restoration of locomotive capability, which was seen in the first set of experiments using acute dopamine depletion, was also observed in chronically lesioned animals. This further confirmed the potential of DCS as a therapeutic approach for PD, following extensive nigrostriatal denervation.

In summary, the studies described above demonstrate that stimulation of the dorsal column pathways using epidural implanted bipolar electrodes, a simple, easy to perform, semi-invasive method, can restore locomotive capability in two animal models of PD symptoms: acutely dopamine-depleted mice and rats with dopaminergic neuronal loss. In parallel with the dramatic behavioral improvements, DCS was found to shift activity patterns in the primary motor cortex and in the dorsolateral striatum into a state closely resembling that found prior to and during initiation of locomotion in normal and depleted animals. Based on these findings, it is proposed that DCS helps motor related brain areas shift into a permissive state for the initiation of movements, in part by effectively desynchronizing cortical and striatal activity patterns. This notion is also supported by the fact that both spontaneous locomotion and locomotion triggered by DCS displayed the same electrophysiological characteristics and similar latency in the onset of locomotion in relation to the preceding shift in neuronal activity patterns. The effect of DCS on motor related brain areas recorded in the present study may involve activation of brainstem arousal systems (Fanselow et al, J. Neurosci. 20:8160 (2000)) and/or direct activation of the involved neuronal circuits through the lemniscal/thalamic pathways. Still, as neither air-puffs alone nor stimulation of trigeminal nerve afferents induced locomotion, even though both stimuli clearly caused an arousal response in the animals, it is unlikely that activation of arousal systems alone can explain the effect of DCS.

The electrophysiological data suggest possible mechanisms for the success of DCS in the treatment of PD, based on existing theories of basal ganglia pathology in PD and specifically considering the circuitry known to be involved in initiating voluntary locomotion (FIG. 22). The command to the spinal cord to initiate locomotion, via reticulospinal pathways, is issued by the diencephalic and mesencephalic locomotor regions. However, a prerequisite for these midbrain structures to become active and trigger locomotion is that they are disinhibited by the output nuclei of the basal ganglia, which in turn need to be disinhibited by striatum (Grillner et al, Trends Neurosci. 28:364 (2005)). Under normal circumstances, the cortex has a powerful excitatory influence on the striatum. In contrast, with reduced striatal dopamine levels, the activation threshold of the projection neurons from the striatum is significantly increased (Grillner et al, Brain Res. Rev. 57:2 (2008)), making it less likely that cortical input to the striatum will be conveyed through this pathway disinhibiting basal ganglia output nuclei. As a consequence, brainstem motor regions remain under tonic inhibition, and the initiation of goal directed locomotion and other types of volitional motor activity become impaired. In this context, DCS may exert its effect by activating large cortical areas, increasing the cortical and thalamic input to the striatum. This may in turn, promote the depolarization and, consequently, facilitate the activation of striatal projection neurons. Another important consequence of the reduced cortical control of striatum at low dopamine levels is that both thalamic and internally driven striatal low-frequency oscillations become more prominent in this situation (Smith et al, Trends Neurosci. 27:520 (2004), Wilson, Neuron 45:575 (2005)). These oscillations may lead to increased synchronicity because the generation of action potentials tends to occur at distinct phases of the LFP oscillation (Costa et al, Neuron. 52:359 (2006), Berke et al, Neuron 43:883 (2004)). This was confirmed in the experiments in which both motor cortex and striatum showed excessive low-frequency synchronized oscillatory activity in dopamine-depleted animals and an increased entrainment of spikes to low-frequency components of the LFPs. Accumulating evidence indicates that such synchronous activity interferes with normal information processing in these circuits and should be considered pathogenic in PD (Hammond et al, Trends Neurosci. 30:357 (2007)). In the data presented here, it is shown that DCS effectively abolishes aberrant synchronous low-frequency oscillations. It is, therefore, tempting to speculate that the suppression of low-frequency oscillations is particularly important for amelioration of motor symptoms in PD. The notion that a certain suppression of low-frequency oscillatory activity is necessary for the initiation of voluntary movements also has some support from previous studies investigating basal ganglia activity during other types of volitional movements (Kuhn et al, Brain 127:735 (2004), Courtemanche et al, J. Neurosci. 23:11741 (2003), Amirnovin et al, J. Neurosci. 24:11302 (2004)).

Finally, a particularly important finding in this study was the demonstration that the combined effect of L-DOPA and DCS allowed for recovery of motor function at significantly lower doses of L-DOPA in severely dopamine-depleted animals. The considerably less invasive nature of the epidural DCS electrode compared to DBS electrodes suggests, therefore, that DCS could be a particularly attractive complement for treatment of symptoms of PD in earlier stages of the disease. In this way, the use of DCS in combination with low levels of L-DOPA could potentially be of great help to large numbers of patients, beginning in the early stages of diagnosis.

All documents and other information sources cited above are hereby incorporated in their entirety by reference.

What is claimed is:

1. A method of continuous therapy for disrupting pathological synchronous neural activity in the brain of a patient suffering from Parkinson's Disease (PD), the method comprising:
    continuously stimulating a peripheral cranial nerve, dorsal sensory roots of spinal nerves, or posterior funiculi of the spinal cord of said patient, wherein the continuous stimulation consists of tonic electrical stimulation under conditions such that said neural activity is disrupted.

2. The method according to claim 1 wherein said electrical stimulation is delivered by an implanted peripheral nerve cuff electrode.

3. The method according to claim 1 wherein said stimulation disrupts pathological synchronous activity in the motor cortex or basal ganglia of said patient.

4. The method according to claim 1 wherein an infraorbital nerve is stimulated.

5. The method according to claim 1 wherein posterior funiculi are stimulated.

6. The method according to claim 5 wherein said stimulation is delivered with electrodes positioned epidurally above the dorsal column of said patient.

7. The method according to claim 1 wherein a trigeminal nerve is stimulated.

8. The method according to claim 7 wherein said trigeminal nerve is stimulated transcutaneously.

9. The method of claim 1, wherein
    said stimulation comprises biphasic square constant current pulses.

10. The method of claim 9 wherein said pulses are emitted at a frequency of 100 to 300 Hz.

11. The method of claim 10 wherein said biphasic pulses have pulse durations between 250 μs and 1 msec.

12. The method of claim 1 comprising continuously stimulating posterior funiculi of the spinal cord of said patient.

13. A method of continuous therapy for disrupting pathological synchronous neural activity in the brain of a Parkinson's disease patient, said method comprising:
    continuously stimulating dorsal sensory roots of spinal nerves or posterior funiculi of the spinal cord of said patient using tonic electrical stimulation via epidural implanted bipolar electrodes under conditions such that said neural activity is disrupted,
    wherein said method does not include acquiring field potential data indicative of a the patient's electrical brain activity in real-time and analyzing the field potential data to identify seizure-related brain activity.

14. The method according to claim 13 wherein said patient is receiving dopamine.

15. A method of restoring locomotive activity in a patient suffering from Parkinson's disease consisting of continuously delivering epidural tonic electrical stimulation to the dorsal column of the spinal cord of said patient under conditions such that said locomotive activity is restored.

16. The method according to claim 15 wherein said stimulation modulates corticostriatal activity.

17. The method according to claim 15 wherein said patient is receiving dopamine.

* * * * *